(12) United States Patent
Karicherla et al.

(10) Patent No.: US 7,448,999 B1
(45) Date of Patent: Nov. 11, 2008

(54) TRANS-SEPTAL INTRA-CARDIAC LEAD SYSTEM

(75) Inventors: Annapurna Karicherla, Valencia, CA (US); Kevin L. Morgan, Simi Valley, CA (US); Gene A. Bornzin, Simi Valley, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 707 days.

(21) Appl. No.: 11/053,468

(22) Filed: Feb. 7, 2005

(51) Int. Cl.
A61B 5/02 (2006.01)
(52) U.S. Cl. .................................... 600/486
(58) Field of Classification Search ............. 607/119, 607/121, 122
See application file for complete search history.

(56) References Cited

U.S. PATENT DOCUMENTS

| | | | |
|---|---|---|---|
| 4,331,156 A | 5/1982 | Apple et al. | |
| 4,485,813 A | 12/1984 | Anderson et al. | |
| 4,712,555 A | 12/1987 | Thornander et al. ... | 128/419 PG |
| 4,788,980 A | 12/1988 | Mann et al. ............ | 128/419 PG |
| 4,913,164 A | 4/1990 | Greene et al. | |
| 4,940,052 A | 7/1990 | Mann et al. ............ | 128/419 PG |
| 5,025,786 A | 6/1991 | Siegel | |
| 5,300,107 A | 4/1994 | Stokes et al. | |
| 5,353,800 A | 10/1994 | Pohndorf et al. | |
| 5,466,254 A | 11/1995 | Helland ..................... | 607/123 |
| 5,476,483 A | 12/1995 | Bornzin et al. ............ | 607/17 |
| 5,796,044 A | 8/1998 | Cobian et al. | |
| 5,810,014 A | 9/1998 | Davis et al. | |
| 5,855,592 A | 1/1999 | McGee et al. | |
| 5,871,531 A | 2/1999 | Struble | |
| 5,921,935 A | 7/1999 | Hickey | |
| 6,309,350 B1 * | 10/2001 | VanTassel et al. ........... | 600/300 |
| 6,328,699 B1 * | 12/2001 | Eigler et al. ................ | 600/486 |
| 6,746,404 B2 | 6/2004 | Schwartz | |
| 6,876,885 B2 | 4/2005 | Swoyer et al. | |
| 7,149,587 B2 | 12/2006 | Wardle et al. | |
| 2002/0055764 A1 | 5/2002 | Malonek et al. | |
| 2002/0111662 A1 | 8/2002 | Iaizzo et al. | |
| 2002/0120200 A1 * | 8/2002 | Brockway et al. ........... | 600/488 |

(Continued)

FOREIGN PATENT DOCUMENTS

WO    WO 03/037428 A2    5/2003

(Continued)

OTHER PUBLICATIONS

NonFinal Office Action, mailed Sep. 13, 2006: Related U.S. Appl. No. 11/053,374.

(Continued)

*Primary Examiner*—Carl H. Layno
*Assistant Examiner*—Jon-Eric Morales

(57) ABSTRACT

An apparatus for and method of measuring pressure through a septum in a patient's heart is disclosed. A lead inserted into the right side of a heart is routed through the septum to gain access to the left side of the heart. The lead includes an attachment structure that secures the lead to one or both of the septal walls. The attachment structure may include at least one protruding tine, membrane, inflatable balloon, involuted spiral or J-lead that engage one or more sides of the septum. The lead also includes one or more sensors for measuring cardiac pressure on the left side of the heart and, as necessary, the right side of the heart.

3 Claims, 23 Drawing Sheets

U.S. PATENT DOCUMENTS

| | | |
|---|---|---|
| 2002/0138009 A1 | 9/2002 | Brockway |
| 2002/0161423 A1 | 10/2002 | Lockhoff et al. |
| 2003/0055344 A1 | 3/2003 | Eigler et al. |
| 2003/0195600 A1 | 10/2003 | Tronnes et al. |
| 2003/0195602 A1 | 10/2003 | Boling |
| 2003/0199779 A1 | 10/2003 | Muhlenberg et al. ........ 600/513 |
| 2003/0199934 A1 | 10/2003 | Struble et al. ................ 607/17 |
| 2003/0199962 A1 | 10/2003 | Struble et al. |
| 2004/0116992 A1 | 6/2004 | Wardle et al. |
| 2004/0147969 A1 | 7/2004 | Mann et al. |
| 2004/0187875 A1 | 9/2004 | He et al. |
| 2004/0215307 A1 | 10/2004 | Michels et al. |
| 2004/0230283 A1 | 11/2004 | Pinzen et al. |
| 2005/0043616 A1* | 2/2005 | Chinchoy .................. 600/431 |
| 2005/0065589 A1 | 3/2005 | Schneider et al. |
| 2005/0165456 A1 | 7/2005 | Mann et al. |
| 2006/0041300 A1 | 2/2006 | Zhang et al. |
| 2006/0064135 A1 | 3/2006 | Brockway |
| 2006/0116590 A1 | 6/2006 | Fayram et al. |

FOREIGN PATENT DOCUMENTS

| | | |
|---|---|---|
| WO | WO 03/037428 A3 | 5/2003 |
| WO | WO 03/089056 A1 | 10/2003 |

OTHER PUBLICATIONS

Final Office Action, mailed Aug. 22, 2007: Related U.S. Appl. No. 11/053,374.

NonFinal Office Action, mailed Oct. 31, 2006: Related U.S. Appl. No. 11/053,518.

Final Office Action, mailed Apr. 20, 2007: Related U.S. Appl. No. 11/053,518.

NonFinal Office Action, mailed May 31, 2007: Related U.S. Appl. No. 11/053,518,

NonFinal Office Action, mailed May 23, 2007: Related U.S. Appl. No. 11/053,493.

NonFinal Office Action, mailed Nov. 1, 2006: Related U.S. Appl. No. 11/053,494.

Final Office Action, mailed Apr. 20, 2007: Related U.S. Appl. No. 11/053,494.

Advisory Office Action, mailed May 30, 2007: Related U.S. Appl. No. 11/053,494.

NonFinal Office Action, mailed Jul. 25, 2007: Related U.S. Appl. No. 11/053,494.

NonFinal Office Action, mailed Feb. 5, 2007: Related U.S. Appl. No. 11/053,566.

NonFinal Office Action, mailed Dec. 28, 2006: Related U.S. Appl. No. 11/053,373.

Final Office Action, mailed Apr. 5, 2007: Related U.S. Appl. No. 11/053,373.

Notice of Allowance, mailed May 31, 2007: Related U.S. Appl. No. 11/053,373.

NonFinal Office Action, mailed Oct. 31, 2007: Related U.S. Appl. No. 11/053,374.

Final Office Action, mailed Sep. 24, 2007: Related U.S. Appl. No. 11/053,493.

Notice of Allowance, mailed Oct. 22, 2007: Related U.S. Appl. No. 11/053,493.

NonFinal Office Action, mailed Oct. 18, 2007: Related U.S. Appl. No. 11/053,494.

NonFinal Office Action, mailed Oct. 1, 2007: Related U.S. Appl. No. 11/053,566.

Notice of Allowance, mailed May 1, 2008: Related U.S. Appl. No. 11/053,374.

Advisory Action, mailed Apr. 7, 2008: Related U.S. Appl. No. 11/053,518.

Final Office Action, mailed Apr. 14, 2008: Related U.S. Appl. No. 11/053,494.

NonFinal Office Action, mailed Dec. 26, 2007: Related U.S. Appl. No. 11/053,566.

* cited by examiner

FIG. 10
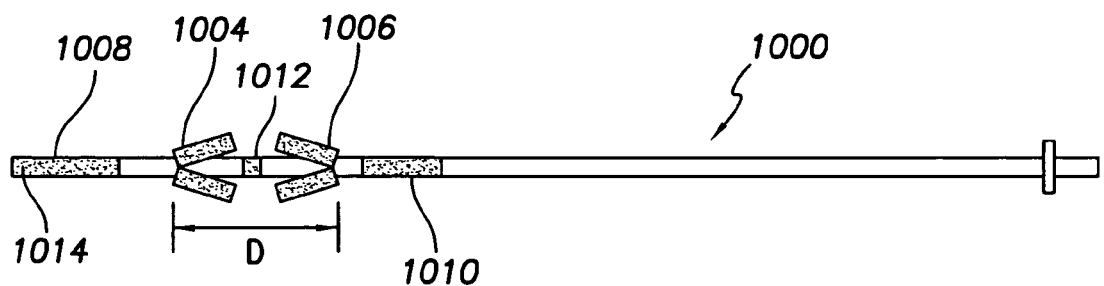
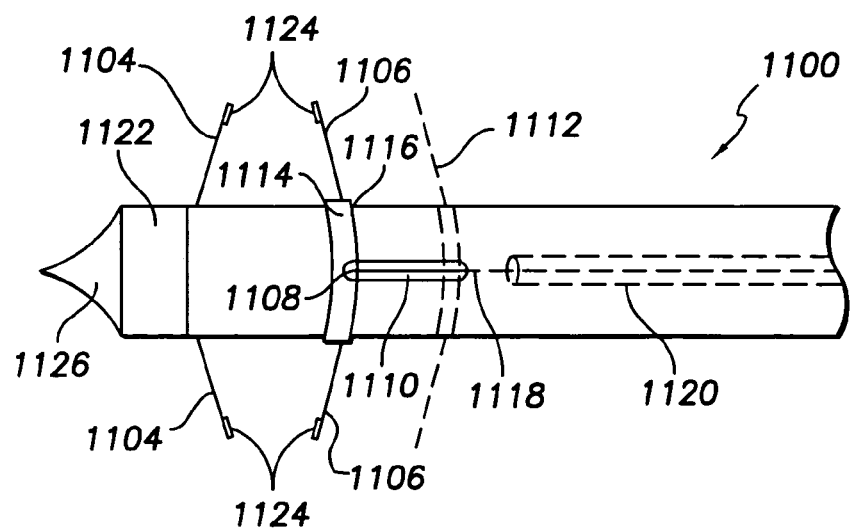
FIG. 11

TRANS-SEPTAL INTRA-CARDIAC LEAD SYSTEM

CROSS REFERENCE TO RELATED APPLICATIONS

This application is related to copending U.S. patent applications:

1) Ser. No. 11/053,374, titled "Trans-Septal Intra-Cardiac Lead System";

2) Ser. No. 11/053,518, titled "Trans-Septal Intra-Cardiac Lead System";

3) Ser. No. 11/053,493, titled "Trans-Septal Intra-Cardiac Lead System";

4) Ser. No. 11/053,494, titled "Trans-Septal Intra-Cardiac Lead System";

5) Ser. No. 11/053,566, titled "Trans-Septal Intra-Cardiac Lead System"; and

6) Ser. No. 11/053,373, titled "Trans-Septal Intra-Cardiac Lead System";

all applications filed concurrently herewith.

TECHNICAL FIELD

This application relates generally to implantable cardiac stimulation devices and, more specifically, to a lead system implanted through a septal wall.

BACKGROUND

When a person's heart does not function normally due to, for example, a genetic or acquired condition various treatments may be prescribed to correct or compensate for the condition. For example, pharmaceutical therapy may be prescribed for a patient or a pacemaker may be implanted in the patient to improve the operation of the patient's heart.

In conjunction with such therapy it may be desirable to measure pressure in one or more chambers of the heart. For example, absolute cardiac pressure may be used as an indicator for several potentially lethal cardiac conditions. By measuring cardiac pressure, abnormal conditions such as these may be detected and in some cases the patient's therapy may be modified to compensate for the abnormal conditions. As an example, if cardiac pressure is continuously measured, the operation of an implanted device such as a pacemaker may be adjusted, as necessary, according to conditions diagnosed as a result of the pressure measurements.

Conventionally, pressure sensing devices have been used to measure pressures on the right side of the heart. However, measurements of right side pressure may not provide sufficient indications for detection of conditions such as congestive heart failure, hypertension and mitral valve defects. In particular, left atrial pressure has been identified as an excellent indicator for left ventricular failure.

Obtaining pressure measurements from the left side of the heart presents several challenges. First, access to the left side of the heart must be provided in a safe manner. In addition, the pressure sensors need to be implanted in a manner that ensures accurate pressure measurements may be made. Again, the use of a safe implantation technique is a primary consideration. Accordingly, a need exists for improved structures and techniques for measuring cardiac pressure.

SUMMARY

The invention relates to an apparatus for and method of measuring pressure through a septal wall in a patient's heart. For convenience, an embodiment of a pressure measurement apparatus constructed according to the invention will be referred to herein simply as an "embodiment."

In one aspect of the invention, a lead inserted into the right side of a heart is routed through a septal wall to gain access to the left side of the heart. The lead includes an attachment structure that secures the lead to the septal wall. The lead also includes one or more sensors for measuring cardiac pressure on the left side of the heart and, if needed, the right side of the heart.

In some embodiments the attachment structure is adjustable to facilitate positioning the attachment structure against one or more septal walls. For example, an attachment structure may include two structures that are positioned on respective sides of a septum. The position of one or both of these structures relative to the lead may then be adjusted to place each structure against a respective septal wall. The lead also may include structure (e.g., a spring) to bias the attachment structure against the walls of the septum to automatically adjust the lead to the thickness of the septal wall.

In some embodiments the attachment structure includes tines that expand outwardly from the distal portion of the lead to engage a side of the septal wall. Again, the lead includes one or more pressure sensors at or near the distal end of the lead to obtain pressure measurements from the left side of the heart and, if applicable, the right side of the heart.

In some embodiments the attachment structure includes one or more flexible membranes that expand outwardly from the lead. Each flexible membrane is then positioned against a side of the septal wall. In this way, the lead may be effectively secured to the septal wall, particularly once the intima is formed. The flexible membrane may include a diaphragm that conducts pressure waves from the left side of the heart to a pressure sensor in the lead via a fluid-filled chamber (e.g., a lumen).

In some embodiments the attachment structure includes one or more inflatable membranes that expand outwardly from the lead. For example, the lead may include a pair of balloon-like structures that are positioned adjacent to the septal wall on opposite sides of the septal wall. Once the balloons are inflated, the lead may be effectively secured to the septal wall. The balloon also may include a diaphragm portion that conducts pressure waves from the left side of the heart to a pressure sensor in the lead via a liquid-filled chamber.

In some embodiments the attachment structure includes one or more involuted spirals that expand outwardly from the distal portion of the lead to engage a side of the septal wall. Again, the lead includes one or more pressure sensors at or near the distal end of the lead to obtain pressure measurements.

In some embodiments the lead includes a J-lead structure on its distal end for securing the lead against a septal wall. For example, the lead may be configured to bend at a distal end that is inserted through an opening in a septal wall. In this way, the bent portion serves to prevent the lead from being pulled back through the opening. The lead includes one or more sensors at its distal end for sensing pressure across the septal wall.

In some embodiments additional pressure sensors may be implanted at various locations in the patient to provide relative pressure measurements. For example, a pressure sensor may be implanted in the thoracic cavity to obtain thoracic cavity pressure relative to any of the chambers in the heart.

In some embodiments the lead includes one or more electrodes to provide electrical stimulation to the heart or to sense electrical activity in the heart. For example, electrodes may be positioned on the lead to apply stimulation to or receive signals in the area of the septal wall. These electrodes may be located on or incorporated in, for example, the lead and/or an attachment structure.

BRIEF DESCRIPTION OF THE DRAWINGS

These and other features, aspects and advantages of the invention will be more fully understood when considered with respect to the following detailed description, appended claims and accompanying drawings, wherein:

FIG. 10 is a simplified diagram of one embodiment of a cardiac lead incorporating a tine attachment structure in accordance with the invention;

FIG. 11 is a simplified diagram of one embodiment of an implantable cardiac lead incorporating adjustable tines in accordance with the invention;

FIG. 28 comprising

FIG. 34 comprising

Figure 1:
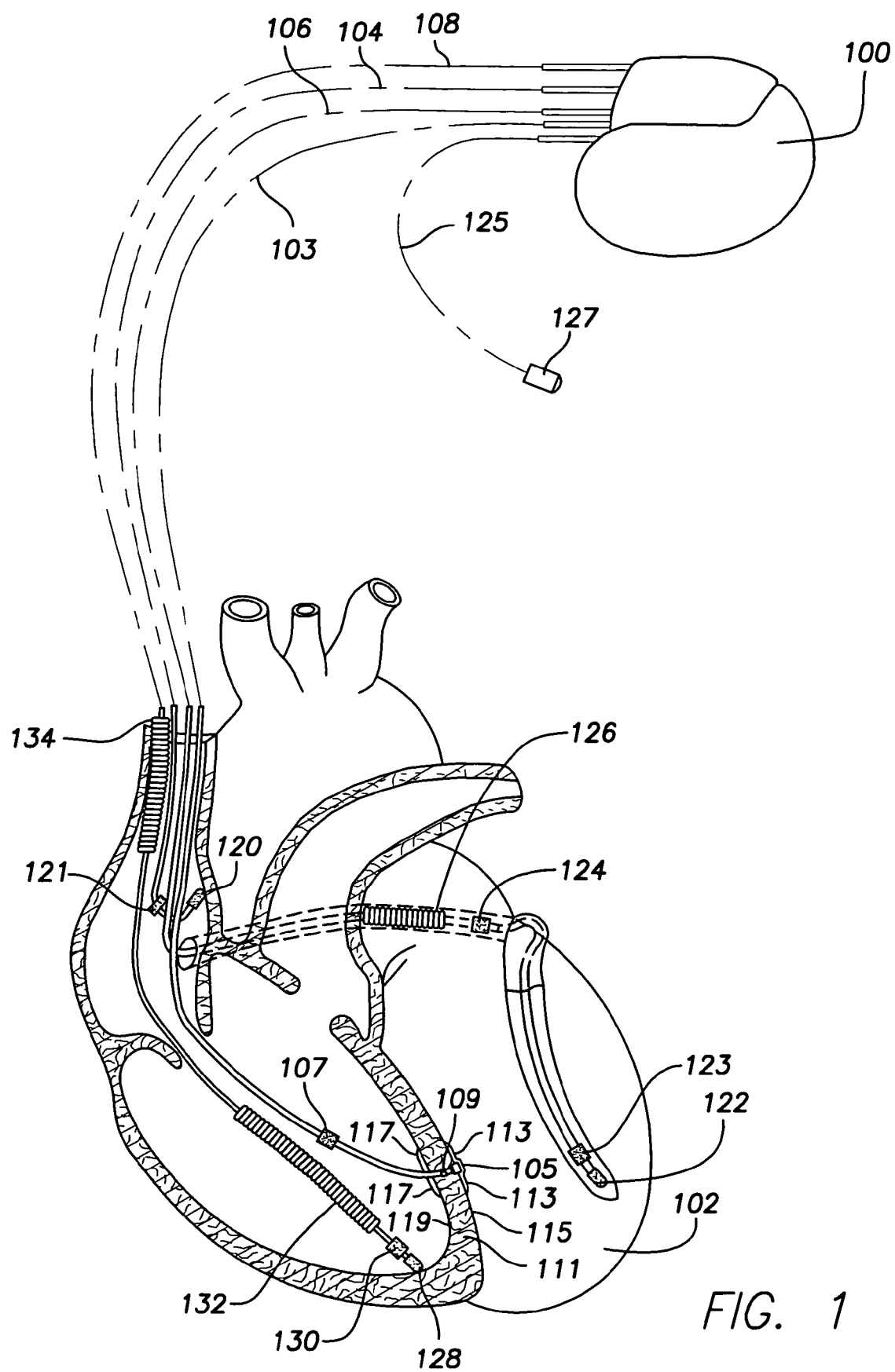
FIG. 1 is a simplified diagram of one embodiment of an implantable stimulation device in electrical communication with several leads implanted in a patient's heart for measuring pressure and delivering multi-chamber stimulation and shock therapy in accordance with the invention.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

Referring to FIG. 1, in one aspect the invention relates to an implantable cardiac device that includes one or more leads (e.g., lead 103) that are implanted in a patient. The lead 103 consists of a lead body and includes sensors 105 and 107 for measuring pressure in the patient and may include one or more electrodes 109 for providing stimulation to or sensing signals in the patient's heart. The implantable cardiac device includes circuitry (e.g., in device 100) that processes signals from the sensors 105 and 107 to determine relative cardiac pressure.

Figure 3:
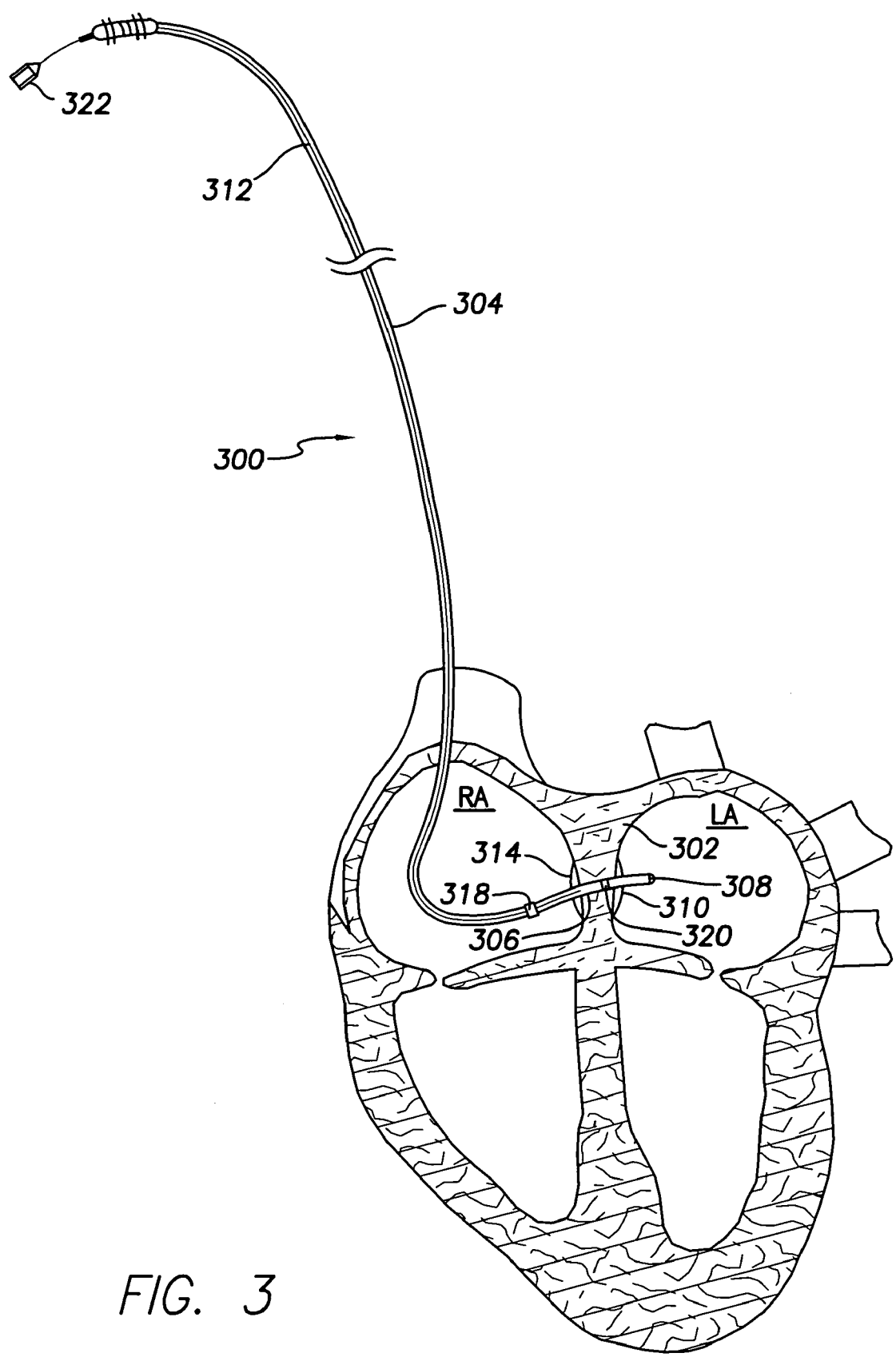
FIG. 3 is a simplified diagram of one embodiment of a cardiac lead having an attachment structure that is implanted through a septum in accordance with the invention.

In embodiments where the lead is initially routed into the right side of the heart, pressure may be measured in the left side of the heart (e.g., the left atrium, left ventricle or aorta) by routing the lead through a wall in the heart (e.g., the ventricular septum 111 or the atrial septum 302 shown in FIG. 3). For example, a hole may be created in the septum by piercing the septum using a separate piercing device or using a lead 103 that has a piercing end.

After a distal portion of the lead 103 is maneuvered through the septum 111, an attachment structure 113 that expands from the lead 103 is positioned against a wall 115 of the septum 111. An attachment structure may take many forms including, without limitation, one or more tines, flexible membranes, inflatable membranes, circumferential tines and/or J-leads. In some embodiments the lead 103 includes another attachment structure 117 that is positioned against another wall 119 of the septum 111.

In one aspect of the invention, an attachment structure is configured so that it has a relatively low profile against the septal wall. In this way, problems associated with protruding objects in the side of the heart may be avoided. For example, blood clots may form on an object that protrudes from a wall of the heart. If these blood clots break loose in the left side of the heart the blood clots may travel to other areas of the body such as the brain and cause a blockage in a blood vessel (i.e., an embolism).

In contrast, the body may quickly build up a biological layer of endothelial cells ("the intima") over an attachment structure with a relatively low profile. As a result, the likelihood of blood clots breaking loose may be significantly reduced as compared to leads that protrude relatively deeply into the left side of the heart.

The buildup of the intima also may assist in firmly attaching the attachment structure to the septal wall. As a result, the lead may be attached to the heart in a sufficiently stable manner so as to prevent injury to the heart and provide accurate pressure measurements.

Through the use of leads that provide a secure and safe attachment to the septal wall and, in some case, other leads and sensors (e.g., lead 125 and sensor 127) implanted in the patient, the implantable cardiac device may be used to provide a variety of pressure measurements in real time. These cardiac pressure measurements may provide valuable information for diagnosing a variety of cardiac problems. Table 1 lists several examples of cardiac problems that may be associated with low or high pressure measurements in the left atrium ("LA"), right atrium ("RA"), left ventricle ("LV") or right ventricle ("RV").

TABLE 1

|  | LA | RA | LV | RV |
|---|---|---|---|---|
| High pressure detected | Mitral stenosis; LV failure | Atrial septal defects | Mitral regurgitation; Aortic regurgitation; Congestive heart failure; HOCM; Septal infarction; Hypertension | Tricuspid regurgitation; Pulmonary stenosis |
| Low pressure detected |  |  | LV failure; Ventricular septal defect; Congestive heart failure | Tricuspid stenosis |

When diagnoses such as these are used in conjunction with a heart stimulation device, appropriate therapy such as cardiac resynchronization therapy may be immediately delivered to the patient. Additional details of an exemplary stimulation device will be discussed in conjunction with FIGS. 1 and 2.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left ventricular ring electrode 123, left atrial pacing therapy using at least a left atrial ring electrode 124, and shocking therapy using at least a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
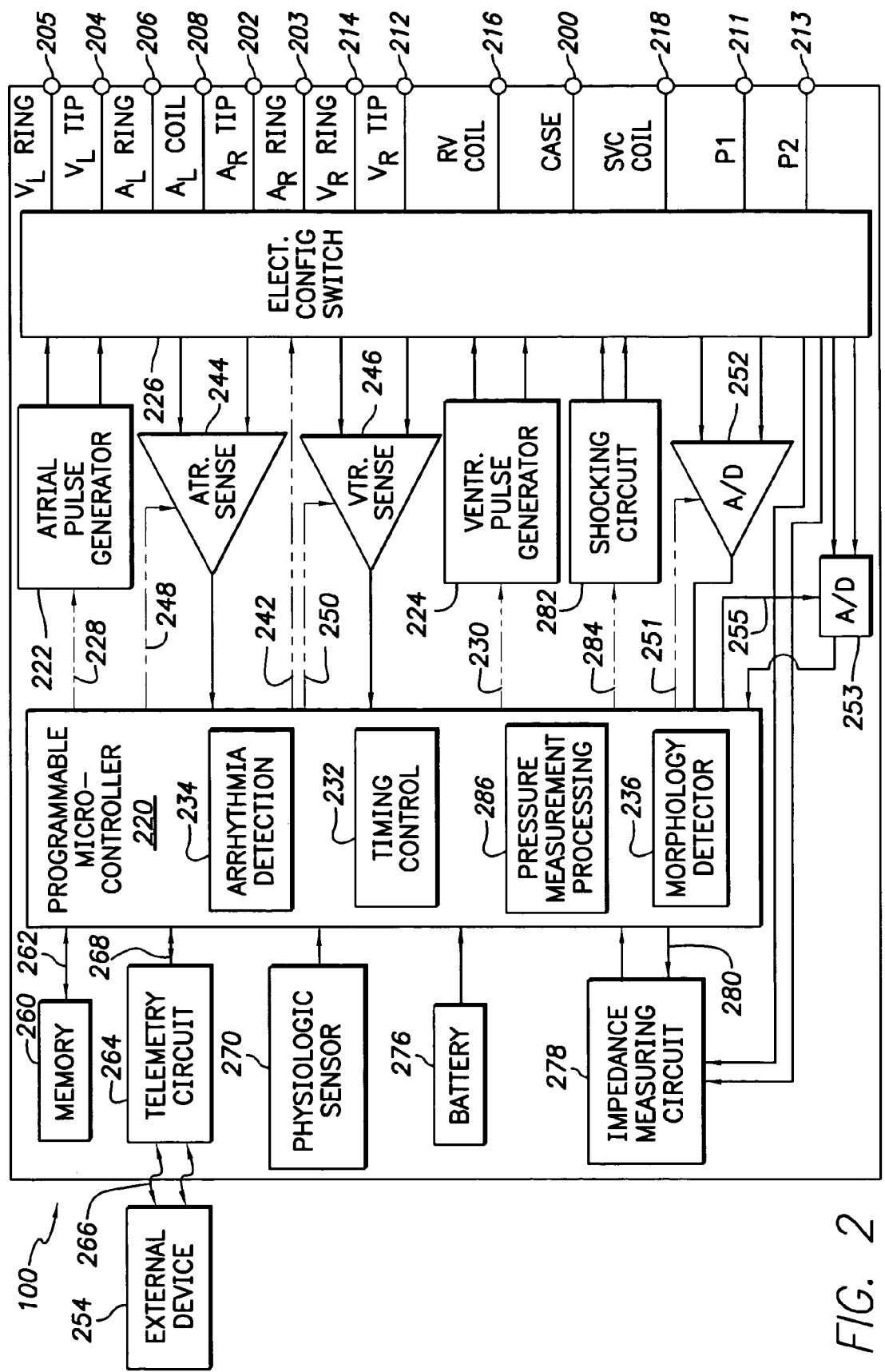
FIG. 2 is a simplified functional block diagram of one embodiment of a multi-chamber implantable stimulation device constructed in accordance with the invention, illustrating basic elements that are configured to provide pressure sensing, cardioversion, defibrillation or pacing stimulation or any combination thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes at least a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart.

Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J to 2.0 J), moderate (e.g., 2.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Pressure Sensors and Related Components

In some embodiments device 100 also may include circuitry for processing signals from one or more pressure sensors. Depending upon the application, the pressure sensors may be implanted in the heart, in other locations in the patient such as the thoracic cavity, anywhere along a lead or within the housing 200.

A typical pressure sensor generates electrical signals indicative of changes in a sensed pressure. Thus, one or more wires may be used to connect a sensor to the device 100. FIG. 2 illustrates an embodiment where two pressure signals P1 and P2 are coupled to the device 100 via terminals 211 and 213, respectively. An analog-to-digital (A/D) data acquisition system 253 may be configured (e.g., via signal line 255) to acquire and amplify the signals P1 and P2, convert the raw analog data into a digital signal, filter the signals and store the digital signals for later processing by, for example, a pressure measurement processing component 286 and/or telemetric transmission to an external device 254.

Referring now to FIGS. 3-7, various embodiments of leads that incorporate an attachment structure on their distal portion for fixing the lead to a wall in the heart will be discussed. FIG. 3 depicts one example of how a lead may be implanted through a septum (the atrial septum in this example) in the heart. FIGS. 4-7 depict several embodiments of leads and illustrate various components that may be incorporated into a lead.

In general, the attachment structure is positioned against the wall in a manner that may prevent the lead from moving relative to the wall. In this way, the attachment structure serves to effectively attach the lead to the wall.

The leads include a sensor and, in some embodiments, components associated with a sensor (hereafter collectively referred to as a sensor for convenience) on their distal portions. This sensor may be entirely or partially positioned in the left side of the heart when the lead is implanted. In this way the lead may be used to monitor pressure in the left side of the heart.

In FIG. 3 a lead 300 includes a lead body 304 that may house one or more electrical conductors, fluid-carrying lumens and/or other components (not shown). The distal end of the lead 300 may be initially introduced into the heart via the right atrium ("RA") using known techniques. For example, the lead 300 may contain a stylet 312 that enables the lead 300 to be manipulated in a desired direction in the heart.

To pass the lead 300 through to the left atrium ("LA"), the atrial septal wall may be pierced using, for example, a piercing tool (not shown) or using a lead 300 that includes on its distal end a relatively sharp and hard tip (not shown). In either case the piercing apparatus is manipulated to create an access tunnel 306 in the septum. The access tunnel 306 may be made in the region of the fossa ovalis since this may be the thinnest portion of the atrial septum 302.

The distal portion of the lead 300 is then maneuvered through the atrial septum 302 (e.g., using the stylet) so that all or a portion of a pressure sensor 308 at the distal end of the lead 300 protrudes into the left atrium. In this way, the sensor 308 may be used to accurately measure pressure in the left atrium.

The lead 300 also may include a pressure sensor 318 positioned proximally on the lead from the sensor 308. The sensor 318 may thus be used to accurately measure pressure in the right atrium. The lead 300 includes an attachment structure that serves to attach the lead 300 to the septum 302. The attachment structure may take many forms including, without limitation, one or more tines, flexible membranes, inflatable membranes, circumferential tines and/or J-leads. FIG. 3 represents the attachment structure in a generalized manner. More specific examples of attachment structures are discussed below in conjunction with FIGS. 10-31.

In the embodiment of FIG. 3, the attachment structure includes a first attachment structure 310 and a second attachment structure 314 implanted on opposite sides of the septum.

In other applications a single attachment structure may be implanted on one of the sides of the septum. It should be understood that the components, configurations and techniques described herein may be applicable to an attachment structure that is implanted on one or more sides of a septum.

The first attachment structure 310 is attached to the distal portion of the lead 300. After the first attachment structure 310 is pushed through the access tunnel 306, it expands outwardly from the lead 300 such that it tends to prevent the distal end of the lead 300 from being pulled back through the access tunnel 306. The first attachment structure 310 is then positioned against a septal wall in the left atrium.

The second attachment structure 314 extends outwardly from the lead 300 to help prevent the lead 300 from sliding further down into the left atrium. As FIG. 3 illustrates, the second attachment structure 314 is positioned against a septal wall in the right atrium.

In some embodiments the attachment structures 310 and 314 are positioned a pre-defined distance apart on the lead 300. For example, the lead may be constructed so that the spacing between the attachment structures 310 and 314 is approximately equal to the thickness of the septum in the area of the access tunnel 306.

In some embodiments one or more of the attachment structures 310 and 314 are attached to the lead 300 in a manner that enables the position of the attachment structure to be adjusted. For example, one or both of the attachment structures 310 and 314 may be slidably mounted to the lead 300 so that they may be moved toward one another to firmly place each attachment structure against the septum 302. Such movement of the attachment structures 310 and 314 may be accomplished, for example, by a manual operation (e.g., via a tensile member such as a stylet or a sheath) or automatically through the use of a biasing member (e.g., a spring).

The lead 300 also may include an electrode 320 that may be used to apply stimulation signals to the septum. For example, a circumferential electrode such as a ring electrode may be located between the first and second attachment structures 310 and 314.

FIG. 3 also illustrates that various control apparatus 322 may be attached to the proximal end of the lead 300. For example, mechanisms may be provided for moving stylets or guide wires 312, movable sheaths or other components (not shown) in the lead 300 or for controlling the flow of fluid through lumens in the lead 300. In some applications, the control apparatus 322 may be removed from the lead 300 when the device 100 (not shown) attached to proximal end of the lead is implanted in the patient.

The embodiment of FIG. 3 may provide highly accurate pressure measurements because the right side and left side pressures may be measured using a single intra cardiac lead. As a result, the number of variables affecting the measurements may be significantly reduced using this approach as compared to approaches that measure different pressures using more than one lead. Moreover, as discussed below, by measuring the pressure gradient across two locations, factors such as drift may be less of a problem as compared to conventional systems that measure the pressure gradient by referencing pressure measurements at each location to a vacuum.

By providing accurate left and right atrium pressure information the embodiment of FIG. 3 may be used to diagnose septal defects (pressure gradient in septal defects is approximately zero) or other cardiac conditions in which therapeutic intervention may be required. Moreover, these pressure measurements may be referenced to pressure in other areas. For example, thoracic pressure may be used as a transmural reference.

Finally, as discussed above in conjunction with FIG. 1 a trans-septal lead as taught herein may be used to measure pressures in the left and right ventricles to diagnose various cardiac conditions. Thus, a lead similar to the one described in FIG. 3 and the figures that follow may be implanted across the ventricular septum.

Referring now to FIGS. 4-7, additional details of various embodiments of leads will be described. These examples also describe the attachment structure in a generic form.

Figure 4:
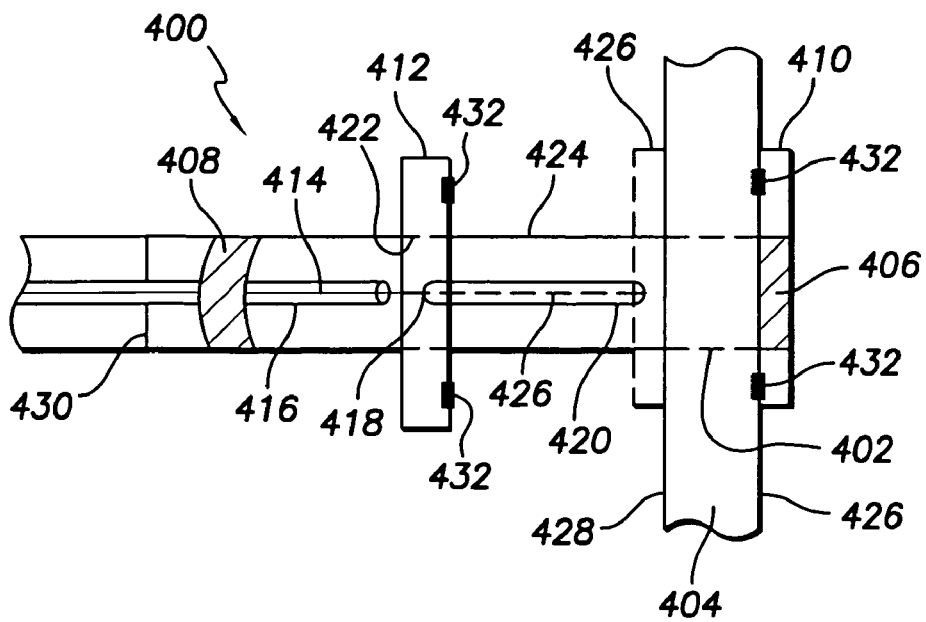
FIG. 4 is a simplified diagram of one embodiment of an implantable cardiac lead incorporating an adjustable attachment structure in accordance with the invention.

In FIG. 4 the distal end of a lead 400 is shown implanted through an access tunnel 402 in a septum 404 (e.g., the atrial or ventricular septum). The lead 400 includes a pressure sensor 406 mounted on the distal end of the lead 400 for measuring pressure in the left side of the heart. The lead 400 also includes a pressure sensor 408 that is used to measure pressure in the right side of the heart.

The lead 400 includes a first attachment structure 410 on its distal end and a second attachment structure 412 mounted proximally on the lead to the first attachment structure 410. The attachment structure 412 is slidably mounted to the lead 400 so that the attachment structure 412 may be moved toward the attachment structure 410 to firmly attach the lead 400 to the septum 404.

Movement of the attachment structure 412 is accomplished by moving a tensile member 414 in a longitudinal direction through the lead 400. In some embodiments, the tensile member 414 may be carried within a lumen 416 that facilitates sliding of the tensile member ("stylet) 414. The proximal end of the tensile member 414 may then be attached to a handle or other structure (not shown) that enables the physician to slide the tensile member 414.

The tensile member 414 attaches to the attachment structure 412 via a fastener mechanism 418. This attachment may be accomplished, for example, using a weld, adhesive, threads or other techniques. In some embodiments the fastener mechanism 418 passes though a slot 420 in the lead 400 so that translational movement of the tensile member 414 causes the attachment structure 412 to slide along the lead 400. In the embodiment of FIG. 4, the attachment structure 412 includes a surface 422 that slides over an outer surface 424 of the lead 400.

The dashed lines 426 represent the position of the attachment structure 412 and the tensile member 414 when the tensile member 414 is slid toward the distal end of the lead 400. In this position, the first and second attachment structures 410 and 412 may be firmly pressed against the septal walls 426 and 428, respectively. In addition, the buildup of the intima also may assist in firmly attaching the attachment structures 410 and 412 to the septal walls.

For embodiments that include an opening (e.g., slot 420) to facilitate translational movement of an attachment structure, the lead 400 also may include a seal 430 that prevents fluid from flowing up the lead 400. Alternatively, the opening (e.g., slot 420) may include a seal that seals around the fastener mechanism 418 to prevent fluid from flowing into the lead 400.

FIG. 4 also depicts an embodiment where one or more of the attachments structures 410 and 412 may include one or more electrodes 432. The electrodes 432 may be used, for example, to pace the septum or to sense signals in the area of the septum.

To reduce the complexity of FIG. 4, the electrical connections and associated conductors for the sensors 406 and 408 and the electrodes 432 are not illustrated. Typically, these electrical conductors will be enclosed in a lumen in the lead 400 that carries the conductors to the device 100 (not shown).

Figure 5:
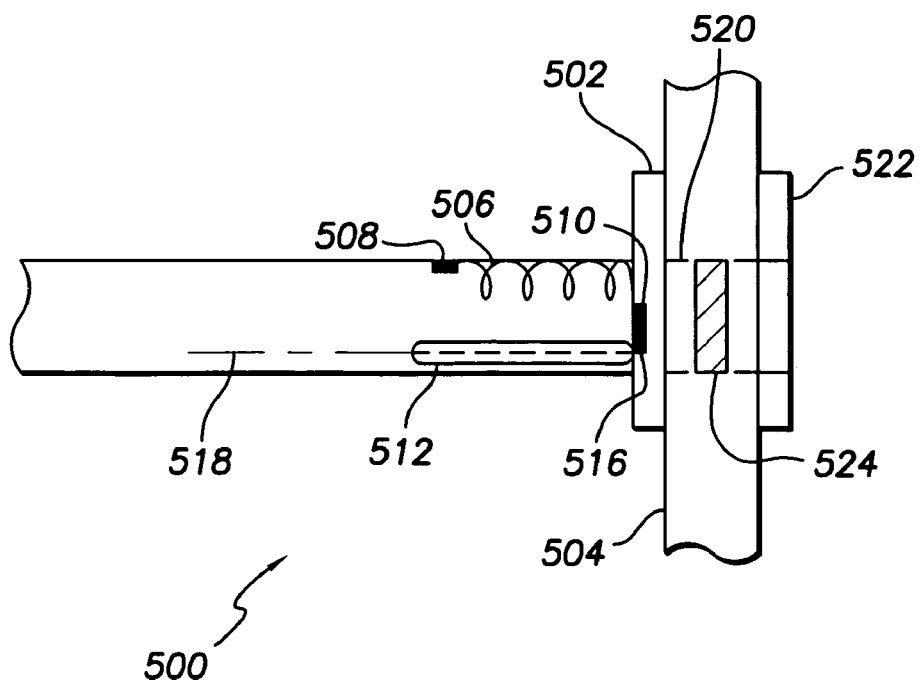
FIG. 5 is a simplified diagram of one embodiment of an implantable cardiac lead incorporating a biased attachment structure in accordance with the invention.

FIG. 5 illustrates the distal end of an embodiment of a lead 500 where an attachment structure 502 is biased toward a septal wall 504 by a biasing member 506 (e.g., a spring). In this case the lead 500 includes a fastener mechanism 508 for connecting one end of the biasing member 506 to the lead 500. In addition, a fastener mechanism 510 facilitates connection of the other end of the biasing member 506 to the attachment structure 502.

As discussed above in conjunction with FIG. 4, the lead 500 may include an opening 512 that accommodates a protrusion 516 of the fastener mechanism 510 such that translational movement of one end of the biasing member 506 causes translational movement of the attachment structure 502 along the lead 500.

In some embodiments, the lead 500 may include a tensile member 518 that may be used to pull the attachment structure 502 away from the distal end of the lead 500. This may be used, for example, to pull the attachment structure 502 away from the septal wall 504 when the distal end of the lead 500 is being inserted into the access tunnel to place an attachment structure 522 in the left side of the heart. After the attachment structure 522 is in place, the tensile member 518 may be released to enable the biasing member 506 to bias the attachment structure 502 against the septal wall 504.

FIG. 5 also illustrates an embodiment where an electrode ring 524 is provided on the circumference of the lead 500. The electrode ring 524 is located between the attachment structures 502 and 522 so that it may come in contact with the septum in the access tunnel 520. The electrode ring 524 may then be used, for example, to pace the septum or sense signals in the septal area.

Figure 6:
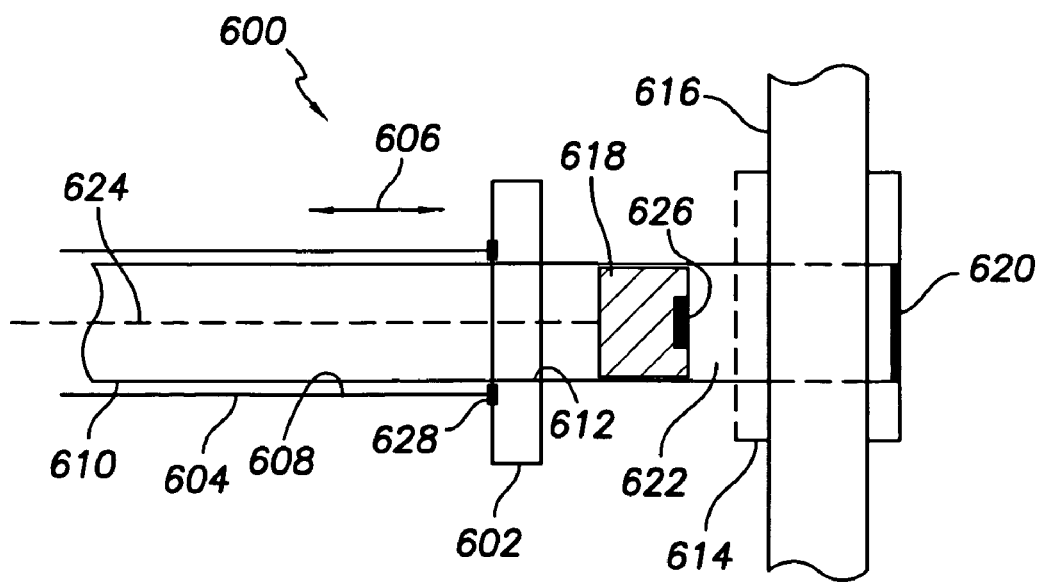
FIG. 6 is a simplified diagram of one embodiment of an implantable cardiac lead incorporating an adjustable attachment structure in accordance with the invention.

FIG. 6 illustrates the distal end of an embodiment of a lead 600 where an attachment structure 602 may be slid along the lead 600 using a sheath 604. The sheath 604 may be provided on the outside of the lead 600 and is configured to slide relative to the lead as indicated by the arrows 606. As illustrated in FIG. 6, an inner surface 608 of the sheath 604 slides on an outer surface 610 of the lead. Similarly, an inner surface 612 of the attachment structure 602 slides on the outer surface 610 of the lead 600. By sliding the sheath 604 toward the distal end of the lead 600, the attachment structure 602 may be positioned (as represented by dashed lines 614) against a septal wall 616.

In some embodiments, the lead 600 includes a fastener mechanism 628 for connecting one end of the sheath 604 to the attachment structure 602. In this way the sheath 604 may move the attachment structure 602 in either direction along the length of the lead 600 as represented by the arrows 606. Alternatively, the sheath 604 may not be attached to the attachment structure 602. In this case, the sheath may be used to push the attachment structure 602 toward the septal wall 616. As is known in the art, the proximal side of the sheath 604 may be attached to a handle or some other structure that facilitates sliding the sheath 604.

FIG. 6 also illustrates an embodiment where a pressure sensor 618 may be placed anywhere along the length of the lead 600. In this case, a flexible diaphragm 620 is provided on the distal end of the lead 600 that protrudes into the left side of the heart. In addition, a chamber 622 filled with a fluid medium is provided between the flexible diaphragm 620 and the pressure sensor 618. Thus, pressure variations in the left side of the heart cause the flexible diaphragm 620 to move which, in turn, creates pressure waves in the fluid medium.

The pressure sensor 618 senses the pressure waves in the fluid medium and generates corresponding electrical signals that are sent to the device 100 (not shown) via one or more electrical conductors 624. In a typical embodiment, the pressure sensor 618 includes a flexible diaphragm 626 and a chip (e.g., a piezoelectric element, not shown) that generates electrical signals in response to pressure waves that are generated inside the sensor when the flexible diaphragm 626 moves. That is, inside the pressure sensor, pressure waves signal are conducted from the flexible diaphragm 626 to the chip.

A variety of fluids or gels may be used in the chamber 622. For example, the fluid may consist of a gas or an incompressible, biocompatible liquid such as water, saline or silicone oil. The gel may be made of a silicone gel, polyacrylamide or any other biocompatible gel. In some applications the fluid and/or gel needs to be compatible with gas sterilization procedures that may be used to sterilize the lead.

The flexible diaphragm 620 may be formed in various shapes and constructed of various materials. For example, the flexible diaphragm may be constructed of a biocompatible material such as silicone rubber, polyurethane or metal. The metal may be, for example, titanium, platinum or Nitinol, and may preferably be thin walled. Shaping of the metal into a bellow allows for a high degree of flexibility for pressure transfer.

Figure 7:
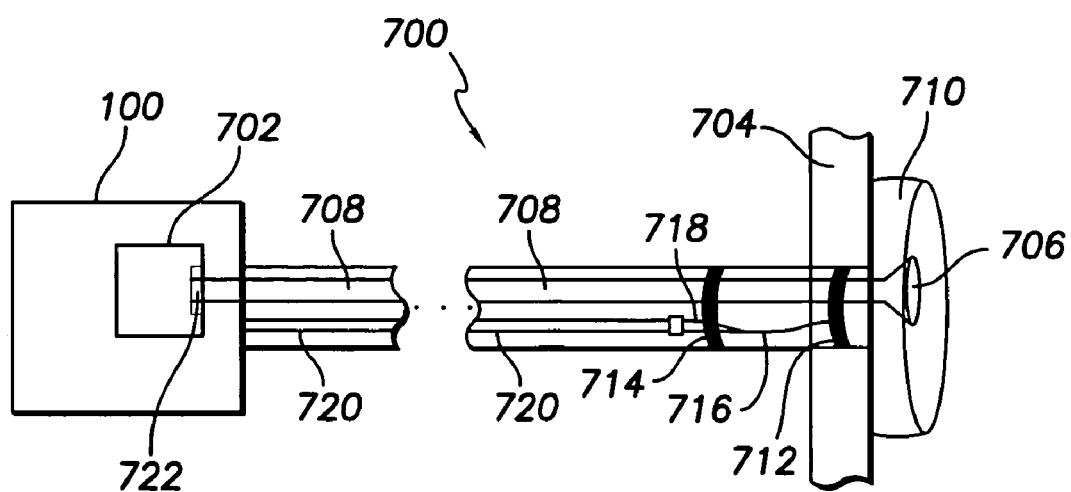
FIG. 7 is a simplified diagram of one embodiment of an implantable cardiac lead incorporating an attachment structure and a flexible diaphragm in accordance with the invention.

FIG. 7 illustrates an embodiment of a lead 700 where a pressure sensor 702 located in the device 100 may measure pressure across a septum 704. The lead 700 includes a flexible diaphragm 706 that may be implanted through the septum into the left side of the heart. As illustrated in FIG. 7, the flexible diaphragm may be attached to attachment structure 710 as discussed herein that serves to fix the lead 700 to the septum 704.

A fluid-filled lumen 708 carries pressure waves from the flexible diaphragm 706 to the sensor 702. The lumen 708 interfaces with the sensor 702 such that pressure waves carried by the fluid in the lumen 708 are provided to a flexible diaphragm 722 in the sensor 702.

FIG. 7 also illustrates the electrical connections between a pair of electrodes 712 and 714 and the device 100. A first electrical conductor 716 is connected to the electrode 712 located to pace/sense the septum area. A second electrical conductor 718 is connected to the electrode 714 that may serve, for example, as the second electrode of a bipolar electrode that includes electrode 712. Both of the conductors 716 and 718 are routed through a lumen 720 through the lead 700 to the device 100.

Figure 8:
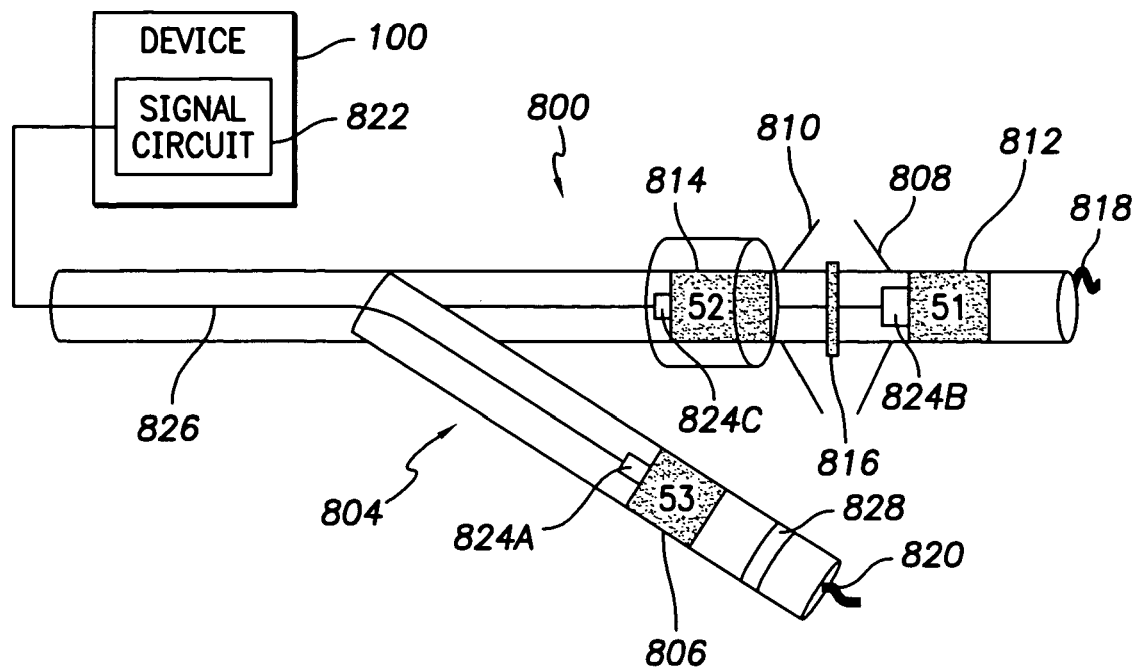
FIG. 8 is a simplified diagram of one embodiment of an implantable cardiac lead incorporating a branch lead in accordance with the invention.
Figure 9:
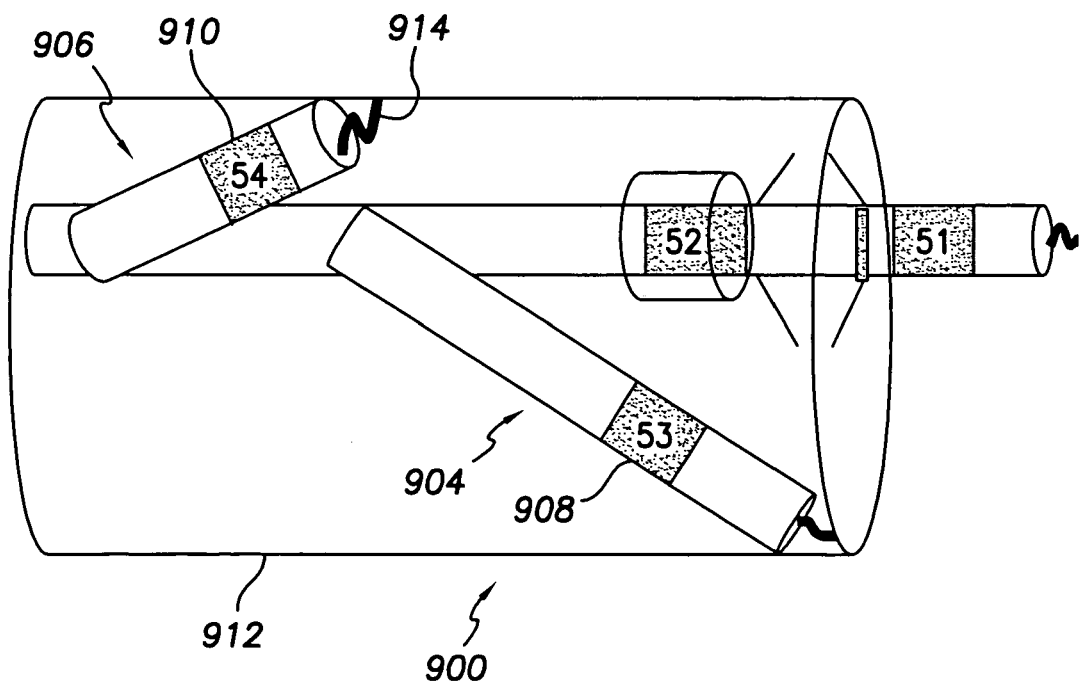
FIG. 9 is a simplified diagram of one embodiment of an implantable cardiac lead incorporating multiple branch leads in accordance with the invention.

Referring now to FIGS. 8 and 9, leads incorporating one or more branch leads will be described. In general, any of the leads and lead components described herein may be used in conjunction with such a lead.

FIG. 8 illustrates an embodiment of a lead 800 that includes a branch lead 804 with a sensor 806. As discussed above, the lead 800 may include components for measuring trans-septal pressure. For example, the lead 800 may include a pair of attachment structures (e.g., tines, flexible membranes, etc.) 808 and 810, a pair of sensors 812 and 814, an electrode 816 and a piercing/tunneling tip 818 at its distal end.

As FIG. 8 illustrates, the sensor 806 may be located at or near the distal end of the branch lead 804. The branch lead 804 also may include a tip 820 (e.g., a boring screw or a set of tines) that facilitates attaching the branch lead 804 to heart tissue. For example, the branch lead 804 may be adapted to be located in the right ventricle to measure right ventricle pressure. In this case the branch lead 804 may be directed into the right ventricle (e.g., via a guide wire), then the tip 820 is manipulated to attach to the wall of the right ventricle to securely fix the branch lead 804 in the right ventricle.

It should be appreciated that such a branch lead may take many forms. For example, the branch lead may include the components described above in conjunction with lead 108 or any other components described herein. For example, a branch lead may include one or more electrodes 828 for pacing or sensing. Also, a branch lead may incorporate one or more of the attachment structures disclosed herein.

FIG. 8 also illustrates that the sensors 806, 812 and 814 may communicate with the device 100 via multiplexed signals. For example, a signal circuit 822 in the device 100 may communicate with signal circuits 824A-C associated with each sensor. These signal circuits may include circuitry that multiplexes and demultiplexes the pressure signals and generates digital or digital-like signals, e.g., pulse wave modulated signals that are sent to the device 100. In this way, the pressure signals may be sent from each of the sensors 806, 812 and 814 to the device 100 via a single connection 826. In addition, the device 100 may send control signals to the sensor circuits 824A-C to, for example, poll the sensors for pressure measurements.

FIG. 9 illustrates an embodiment of a lead 900 that includes two branch leads 904 and 906 having sensors 908 and 910, respectively. The distal portion of the main lead 900 and the branch lead 904 may include components similar to those in the embodiment of FIG. 8.

The sensor 910 may be located at or near the distal end of the branch lead 906. The branch lead 906 also may include a tip 914 (e.g., a boring screw or a set of tines) that facilitates attaching the branch lead 906 to heart tissue. For example, the branch lead 906 may be configured to be located in the right atrium to measure transmural pressure. In this case, branch lead 906 may be directed into the right atrium with the lead 900, then the tip 914 is manipulated to bore into a wall of the right atrium to securely fix the branch lead 906 in the right atrium.

Again it should be appreciated that such a branch lead may take many forms. For example, the branch lead may include the components described above in conjunction with lead 104.

FIG. 9 also illustrates that the lead 900 may include a temporary lumen (e.g., sheath) 912 that holds the branches together during the initial implantation process. Use of a lumen may provide improved maneuverability during lead implant. For example, the lumen 912 may be placed over the branches until the septum lead (e.g., the distal portion of the main lead 900) is implanted. Then the lumen may be drawn back, enabling the branch 904 to be installed in the right ventricle as discussed above in conjunction with FIG. 8. Finally, the lumen 912 may be removed to enable the branch 906 to be implanted in, for example, the right atrium. In some embodiments the construction of the lumen 912 may be similar to that of a catheter used for implanting leads.

It should be appreciated that a variety of lead structures and configurations may be used in accordance with the teachings herein. For example, a typical lead may include separate lumens for housing guide wires and the electrical leads for the sensors and the electrodes. In addition, a lead body (e.g., lead body 304) may be constructed out of a variety of biocompatible materials such as MP35N, platinum, silicone and polyurethane.

Similarly, a variety of different attachment structures may be used in accordance with the teachings herein. For example, one or more attachment structures may be incorporated into a lead. Moreover, a lead may include one or more of the various types attachment structures described herein.

In addition, the attachment structures may be configured to be extendable and/or retractable. This latter configuration may provide, for example, improved maneuverability; particularly when tunneling across the septum.

An attachment structure may be constructed of a variety of materials including, for example, biocompatible materials such as silicone and polyurethane. The attachment structure may be metallic or non-metallic. In some embodiments the attachment structure may be constructed of a biodegradable material that degrades over time. This type of material may be used, for example, in a case where it may be necessary to remove the lead sometime in the future.

The leads may incorporate various types of electrodes and these electrodes may be implemented in various locations on the leads. In general, any of the electrodes described herein may be used in conjunction with the leads described herein.

In addition, a variety of different sensor structures may be used in accordance with the teachings herein. For example, a typical sensor includes a pressure transducer such as a piezoelectric chip that is mounted in a package that has a flexible diaphragm on at least a portion of its outer surface. The package is then incorporated into the intra cardiac lead so that the flexible diaphragm is exposed to a heart chamber or to a fluid-filled lumen or chamber that transmits pressure waves from the heart chamber. Thus, when the pressure changes in the chamber the flexible diaphragm will transmit a pressure wave to the piezoelectric device. The piezoelectric device then generates an electrical signal that may, for example, correspond to the magnitude of the change in pressure. It should be understood, however, that many other forms of sensors may be used in a lead constructed according to the invention. Moreover, in general, any of the sensors described herein may be used in conjunction with the leads described herein.

Referring now to FIGS. 10-13, various embodiments of leads that incorporate one or more tine or tine-like protrusion attachment structures (hereafter referred to as "tines" for convenience) will be discussed. These leads may be implanted through a septum in the heart as discussed above. Collectively, FIGS. 10-13 describe a variety of components that may be incorporated into such a lead.

FIG. 10 depicts a relatively simple embodiment of a lead 1000 that incorporates tines. The distal end of the lead 1000 is on the left side of FIG. 10. The lead 1000 includes two sets of tines 1004 and 1006 that are oriented in opposite directions.

When the lead is implanted, the first set of tines 1004 attached to the distal portion of the lead 1000 is maneuvered through the access tunnel in the septum (not shown). The tines 1004 may be oriented and constructed so that they will collapse when passing through the access tunnel.

After the tines 1004 pass through the access tunnel the tines 1004 may be expanded and then positioned against a septal wall in the left side of the heart (e.g., the left atrium, not shown). In this configuration, the tines 1004 may prevent the lead 1000 from being pulled back out of the access tunnel. For example, after the tines 1004 have passed into the left side of the heart, pulling the lead 1000 back toward the right side of the heart may cause the tines 1004 to open when they contact the septal wall. As a result, the tines 1004 will tend to prevent the distal end of the lead 1000 from being pulled back into the right side of the heart.

A second set of tines 1006 extending from the lead 1000 may be positioned against the opposite side of the septal wall (e.g., in the right atrium, not shown). The tines 1006 may help prevent the lead 1000 from extending further into the left side of the heart.

As described in more detail below, the tines 1006 and 1004 may be oriented in opposite directions so that the tines will tend to lock the lead 1000 in place on the septum. For example, the tines 1006 may be oriented so that they will tend to open when they contact the septal wall as the lead 1000 is pushed toward the left side of the heart.

In some embodiments the tines 1004 and 1006 are positioned a given distance D apart on the lead 1000. For example, the lead 1000 may be constructed so that the spacing D between the tines 1004 and 1006 is approximately equal to the thickness of the septum in the area of the access tunnel. In some patients this thickness is approximately 3-4 mm in the area of the fossa ovalis.

The lead 1000 also includes a sensor 1008 for measuring pressure in the left side of the heart, a sensor 1010 for measuring pressure in the right side of the heart, a ring electrode 1012 that may be used for unipolar pacing of the septum and an electrode 1014 that may be used in conjunction with the electrode 1012 for bipolar pacing or sensing. Electrical wires (not shown) in the lead 1000 connect the sensors 1008 and 1010 and the electrodes 1012 and 1014 to the device 100 (not shown).

In some embodiments the tines are slidably mounted to the lead so that the tines may be moved toward one another to firmly attach the lead to the septum. Such movement of the tines may be accomplished, for example, by a manual operation (e.g., via a tensile member or sheath) or automatically through the use of a biasing member (e.g., a spring).

FIG. 11 depicts an embodiment of a lead 1100 that incorporates two sets of tines 1104 and 1106 where the set of tines 1106 is slidably mounted to the lead 1100. In this embodiment the position of the tines 1106 relative to the tines 1104 may be adjusted in a longitudinal direction relative to the lead 1100. In this way the tines 1104 and 1106 may be pressed against opposite septal walls to effectively lock the tines to the septum (not shown).

In some embodiments the slidable attachment consists of one or more tongue structures 1108 on the tines 1106 and one or more corresponding groove structures 1110 on the lead 1100. Thus the tines 1106 may be slid along the groove between the position shown and the position represented by the dashed lines 1112.

In some embodiments, once the slidable tines 1106 are positioned on the lead 1100 they may be held in place (e.g., prevented from sliding) on the lead 1100 by friction between a support structure 1114 for the tines 1106 and a surface 1116 of the lead 1100. Alternatively, an active holding structure (not shown) may be used to fix the position of the tines 1106 relative to the lead 1100.

The lead 1100 may include a tensile member such as a stylet 1118 that slides within the lead 1100 and is attached to the tines 1106 or the support structure 1114. In this case, sliding the tensile member 1118 will cause the tines 1106 to slide toward or away from the tines 1104. As shown in FIG. 11, the stylet may be enclosed in a lumen 1120 in the lead. In addition, a handle (not shown) may be connected to the tensile member 1118 at the proximal end of the lead 1100.

It should be appreciated, however, that other techniques for moving the tines may be used. For example, the lead 1100 may include a sheath (not shown) that slides in a longitudinal direction relative to the lead 1100 as described above in conjunction with FIG. 6. The sheath, in turn, may be attached to the slidable tines 1106. Thus, the tines 1106 may be slid toward the tines 1104 by sliding the sheath. In this way, when the tines 1104 and 1106 are positioned on opposite sides of the septum the tines 1104 and 1106 may be firmly pushed up against respective septal walls. In addition, the applied force may serve to further spread the tines 1104 and 1106 so that the tines 1104 and 1106 will lie flatter against the septal walls. As is known in the art, the proximal side of the sheath may be attached to a handle or some other structure that facilitates sliding the sheath.

In some embodiments the sheath may be releasably attached to the tines 1106 so that the sheath may be withdrawn from the tines 1106 as described above in conjunction with FIG. 6. For example, the sheath may be constructed so that it is not actually attached to the tines 1106, but merely abuts against the proximal side of the tines 1106 to push the tines 1106 toward the distal end of the lead 1100.

The lead 1100 includes one or more sensors to sense pressure on the left side of the heart (sensor 1122) and on the right side of the heart (not shown). Electrical wires (not shown) in the lead 1100 connect the sensors (e.g., sensor 1122) to the device 100 (not shown).

The embodiment of FIG. 11 illustrates that the tines 1104 and 1106 may incorporate electrodes 1124. The electrodes 1124 may be used, for example, to pace the septal walls or sense in the vicinity of the septum. Alternatively, the tines 1104 and 1106 may be constructed of an electrically conductive material (e.g., a biocompatible metal or a conductive polymer) so that the tines 1104 and 1106 also function as electrodes. The conductive polymer may consist of, for example, silicone rubber with conductive micro or nano particles. The particles may comprise, for example, gold, platinum, iridium, carbon nanotubes or titanium. Electrical wires (not shown) in the lead 1100 connect the electrodes 1112 or tines to the device 100 (not shown).

The embodiment of FIG. 11 also illustrates that the lead 1100 may include a relatively sharp distal end 1126. As discussed above, the sharp end 1126 may be used to pierce through the septum to create an access tunnel that enables the distal portion of the lead 1100 to pass into the left side of the heart.

Figure 12:
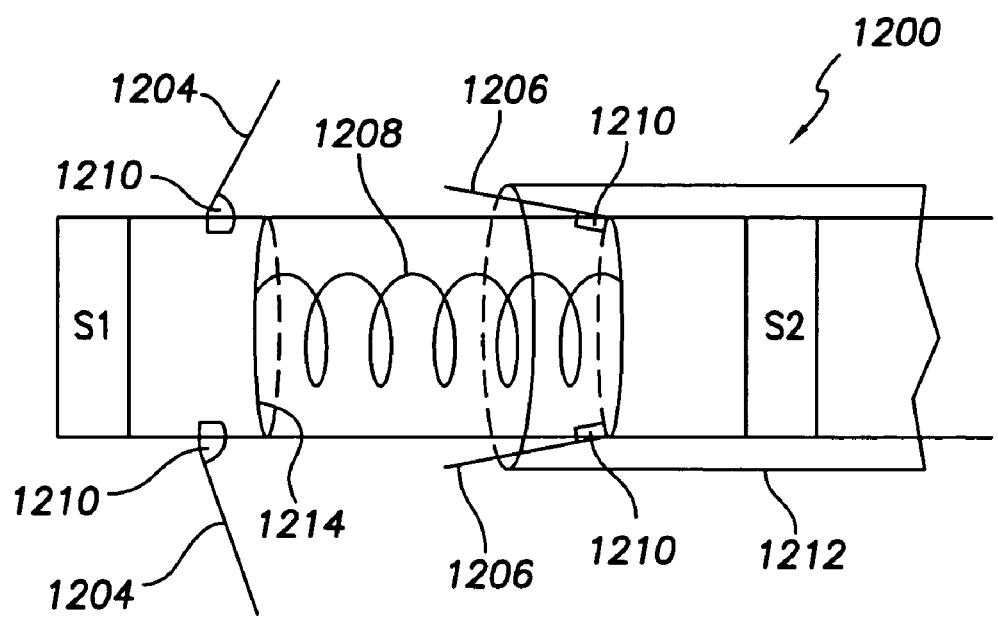
FIG. 12 is a simplified diagram of one embodiment of an implantable cardiac lead incorporating biased tines in accordance with the invention.

FIG. 12 depicts an embodiment of a lead 1200 that incorporates two sets of tines 1204 and 1206 that are biased toward one another by a biasing member. In this embodiment, the second set of tines 1206 is attached to the biasing member and slidably mounted to the lead 1200 (e.g., as discussed above). The biasing member is configured to force the tines 1206 toward the tines 1204. In this way the tines 1204 and 1206 may be biased against opposite septal walls (not shown) to actively lock the tines 1204 and 1206 to the septum. As a result, the spacing between the tines 1204 and 1206 may be automatically adjusted according to the width of the septum. In addition, the force applied by the biasing member may serve to further spread the tines 1204 and 1206 radially from the lead 1200 so that the tines 1204 and 1206 will lie flatter against the septal walls.

In FIG. 12 the biasing member incorporates a spring 1208 that is connected to the slidable tines 1206. The spring 1208 is also connected to the lead 1200 using, for example, a fastener mechanism 1214. As a result, the spring 1208 may bias the tines 1206 towards the tines 1204. Thus, when the tines are expanded (e.g., as depicted for tines 1204) from the lead 1200 on opposite sides of a septum, the spring 1208 may be used to pull the two sets of tines together so that they are firmly held to their respective septal walls.

As another example, in an embodiment that does not use the sheath 1212 discussed below, when the tines 1204 are pushed through the access tunnel the orientation of the tines 1206 may prevent the tines 1206 from passing into the access tunnel. As a result, the spring 1208 will expand as the proximal end of the lead 1200 is pushed further into the access tunnel. After the tines 1204 pass through the access tunnel, they will expand out from the lead 1200. When this happens the physician will release the distal pressure on the lead 1200 and the spring 1208 will pull the two sets of tines 1204 and 1206 toward one another. As a result, the tines will be effectively locked against the septum.

It should be appreciated that other orientations may be used for the biasing member. For example, a spring may be positioned on the right side of the tines 1206. In this case, the spring may attach to the lead 1200 to the right of the tines 1206 in FIG. 12. In addition, the spring may initially be configured to not engage the slidable tines 1206. In this case a trigger mechanism may be used to release the spring to engage the slidable tines 1206.

FIG. 12 also illustrates that the tines 1204 and 1206 may include biasing members 1210 each of which cause one or more of the tines to expand away from the lead 1200. For example the biasing member 1210 may include a relatively simple spring.

Alternatively, the tines 1204 and 1206 may be constructed so that they naturally tend to expand away from the lead 1200. For example, the tines may be made of a piece of elastic metal that is bent to be in an extended position. In this case the elasticity of the metal may permit the tines to be bent to a non-extended position (e.g., a position where the tines lie against the lead) when a force is applied, yet the tines will go back to their original position when the force is removed.

The lead 1200 also may include a sheath 1212 that slides relative to the lead 1200. The sheath 1212 may be used to hold the tines 1204 and 1206 in a non-extended position (e.g., the position depicted for tines 1206) when the lead 1200 is being installed. After the lead 1200 has been properly positioned in the heart, the sheath 1212 may be pulled toward the proximal end of the lead 1200 to release the tines. As mentioned above, the proximal side of the sheath may be attached to a handle or some other structure that facilitates sliding the sheath 1212.

The lead 1200 also include two pressure sensors S1 and S2. As discussed above, these sensors may be used to measure pressure in the left and right sides of the heart.

Figure 13:
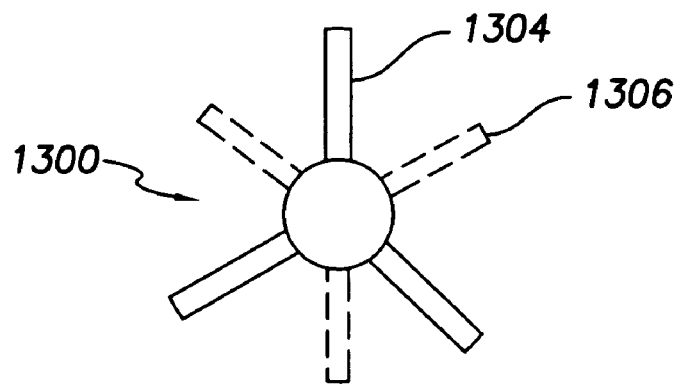
FIG. 13 is an end view of one embodiment of an implantable cardiac lead incorporating tines in accordance with the invention.

FIG. 13 is an end view of two set of tines on a lead 1300 that illustrates that each set of tines may have a different orientation with respect to a cross section of the lead 1300. The orientation of the first set of tines 1304 (e.g., tines 1104 in FIG. 11) is shown using solid lines. The orientation of the second set of tines 1306 (e.g., tines 1106 in FIG. 11) is shown using dashed lines. One advantage of using different orientations for the two sets of tines is that the second set of tines may be less likely to follow the first set of tines through the access tunnel. In addition, the different orientations of the tines may provide a more effective lock across the septum.

A variety of different tines or tine-like structures may be used in accordance with the teachings herein. For example, any number of tines or tine-like protrusions may be used in each set of tines discussed herein.

The tines may be configured to be extendable and retractable. This configuration may provide, for example, improved maneuverability; particularly when tunneling across the septum.

The tines may be constructed of a variety of materials including, for example, biocompatible materials such as silicone and polyurethane. Typically the tines would be non-metallic. In some embodiments the tines may be constructed of a biodegradable material that degrades over time. This type of material may be used, for example, in a case where it may be necessary to remove of the lead sometime in the future.

It should be appreciated that the above embodiments depict but a few examples of the components that may be incorporated into a lead incorporating tines. A variety of other components including for example, those described elsewhere herein, may be incorporated into such a lead. For example, in the illustrated embodiments these leads include a sensor on their distal portions that are positioned in the left side of the heart when the lead is implanted to monitor pressure in the left side of the heart. It should be appreciated, however, that such leads may incorporate other sensor configurations in accordance with the teachings herein.

Figure 14:
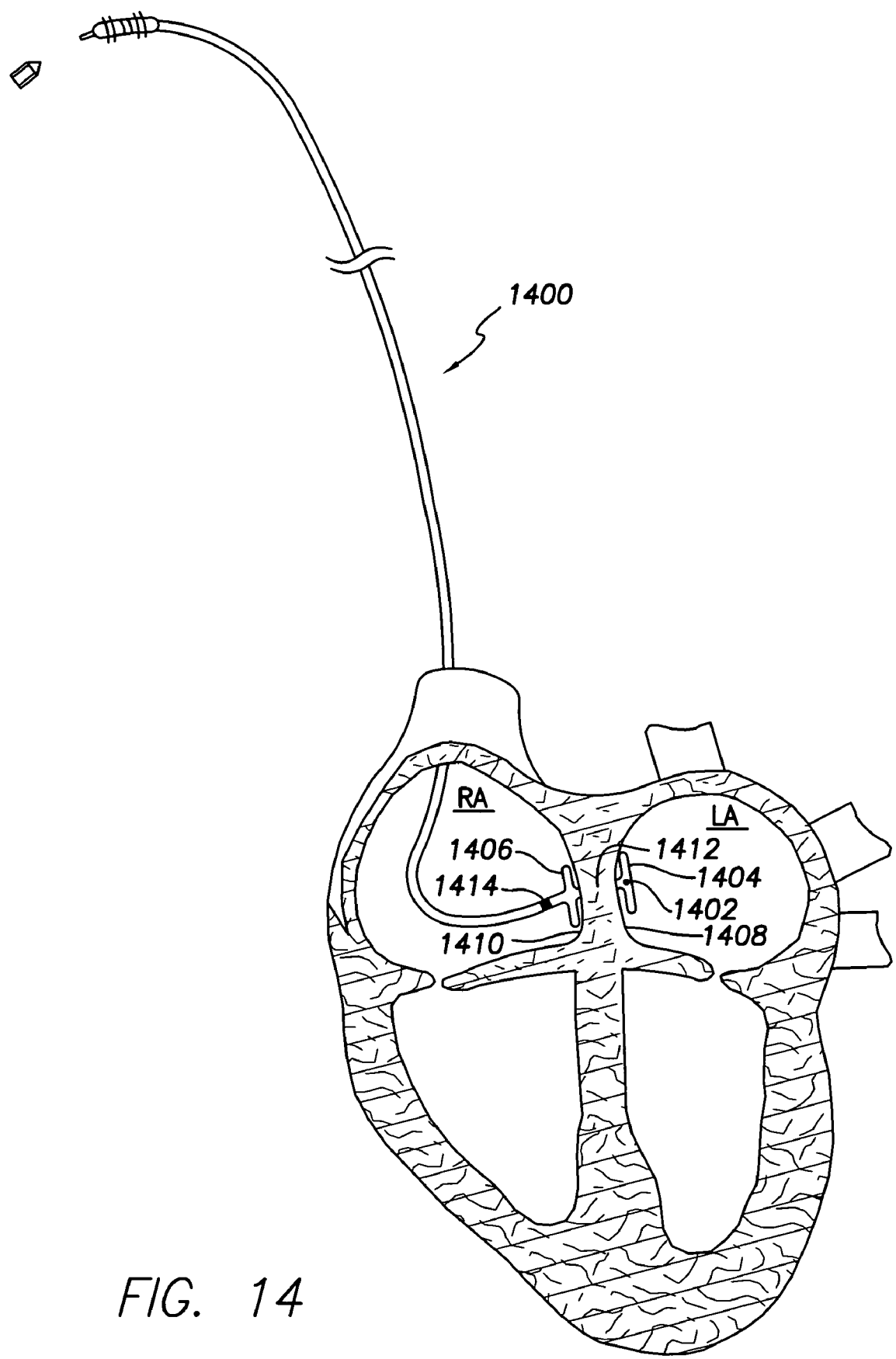
FIG. 14 is a simplified diagram of one embodiment of a cardiac lead having a membrane attachment structure that is implanted through a septum in accordance with the invention.

Referring now to FIGS. 14-19, various embodiments of leads that incorporate one or more disk, membrane or membrane-like attachment structures (hereafter referred to as "membranes" for convenience) will be discussed. FIG. 14 depicts a lead implanted through a septum (the atrial septum in this example) in the heart. FIGS. 15-19 illustrate various components that may be incorporated into a lead.

In FIG. 14, a lead 1400 may be initially introduced into the heart via the right atrium RA as discussed above in conjunction with FIG. 3. The lead 1400 is then passed through to the left atrium after an access tunnel is created in the atrial septal wall using, for example, a piercing tool (not shown). The distal portion of the lead 1400 is then maneuvered through the access tunnel so that a flexible diaphragm 1402 on the distal end of the lead 1400 protrudes into the left atrium LA.

The flexible diaphragm 1402 comprises part of a sensor assembly that measures pressure in the left side of the heart. In some embodiments the flexible diaphragm 1402 comprises part of pressure sensor. In some embodiments the flexible diaphragm 1402 is used to couple pressure waves from the left side of the heart to a sensor in the lead via a fluid-filled chamber (e.g., a lumen).

The distal end of the lead 1400 may include a membrane 1404 that is implanted into the left atrium. In some embodiments the membrane 1404 has sufficient elasticity such that it tends to expand radially outward from the lead 1400. In this way the membrane 1404 may be maneuvered to lie relatively flat against a septal wall 1408 to fix the lead 1400 to the septum.

The lead 1400 may include a membrane 1406 located proximally from the end of the lead 1400. The membrane 1406 also may have sufficient elasticity such that it tends to expand radially outward from the lead 1440. Thus, the membrane 1406 may be maneuvered to lie relatively flat against a septal wall 1410 to fix the lead 1400 to the septum.

The lead 1400 also may include one or more electrodes (e.g., a ring electrode) that are used to apply stimulation signals to the septum or sense signals in the area of the septum. For example an electrode 1412 may be located a short distance away from the proximal side of the membrane 1404 and an electrode 1414 may be located a short distance away from the proximal side of the membrane 1406. The electrode 1412 may, for example, be used for unipolar pacing of the septum or sensing in the septal area. The electrode 1414 may, for example, be used for bipolar sensing of the septum in conjunction with a sensing electrode 1412 or for unipolar sensing. To reduce the complexity of FIG. 14, the electrical connections between the electrodes and the device 100 are not shown.

Figure 15:
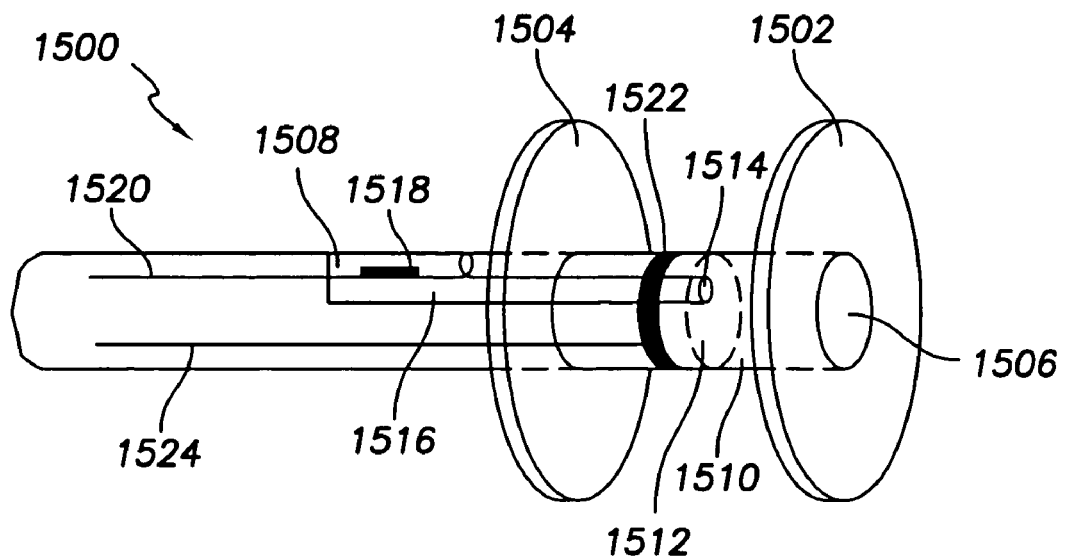
FIG. 15 is a simplified diagram of one embodiment of an implantable cardiac lead incorporating membranes in accordance with the invention.

FIG. 15 depicts the distal end of one embodiment of a lead 1500 incorporating two membrane attachment structures 1502 and 1504. The membrane 1502 is attached to the distal end of the lead 1500. The membrane 1504 is attached to the lead 1500 on the proximal side of membrane 1502. Typically, the distance between the two membranes 1502 and 1504 is approximately equal to the width of the septum in the area of the access tunnel through the septum (not shown).

In some embodiments, (e.g., as discussed herein for other attachment structures) one or both of the membranes 1502 and 1504 may be slidably mounted to the lead 1500. For example, the lead 1504 may slide on the outside of the body of the lead 1500. In addition, a biasing member such as a spring (not shown) may be used as described herein to bias the membranes 1502 and 1504 to automatically adjust to various septal wall thicknesses. These features may enable the membranes 1502 and 1504 to be more firmly placed against the walls of the septum.

The membranes 1502 and 1504 may be constructed to lie relatively flat against a septal wall and to have a relatively low profile. Thus, the membranes 1502 and 1504 may serve to securely attach the lead 1500 to the septum without encroaching too far into the left side of the heart. Due to this low profile and the formation of the intima the likelihood of blood clots breaking loose may be significantly reduced as compared to leads that protrude relatively deeply into the left side of the heart.

The membranes 1502 and 1504 may be constructed using a variety of materials. For example, the membranes 1502 and 1504 may be constructed of silicone, a Dacron mesh or a cloth-like material.

Once the lead 1500 is secured in place (e.g., by appropriate placement and by the formation of the intima), a flexible diaphragm 1506 located at the distal end of the lead 1500 may be used to detect pressure in the left side of the heart. For example, pressure waves from the left side of the heart may be transmitted from the flexible diaphragm 1506 to a sensor 1508 via a fluid-filled chamber 1510 in the lead 1500.

In some embodiments the flexible diaphragm 1506 may be integral with the membrane 1502. For example, the membrane 1502 may be constructed of a flexible material such as silicone such that the distal side wall of the membrane 1502 serves as the flexible diaphragm 1506. Alternatively, the membrane may include a diaphragmatic portion (similar to a drum) that enables the transfer of pressure waves from the left side of the heart to the sensor 1508.

In some embodiments the flexible diaphragm 1506 may be a separate component that is attached to the membrane 1502 and/or the body of the lead 1500. In some embodiments the flexible diaphragm 1506 may be constructed of silicone or a thin metal.

In the embodiment of FIG. 15, an initial fluid-filled chamber defined by a wall 1512 connects via a port 1514 to a lumen 1516 to place the sensor in fluid communication with the flexible diaphragm 1506. In this way, space may be provided in the lead 1500 on the proximal side of the wall 1512 for other components (e.g., electrical conductors). In practice, the chamber may transfer the pressure waves from the flexile diaphragm 1506 to a sensor located at any location along the length of the lead 1500 (e.g., sensor 1508) or located in the device 100 (not shown).

The sensor 1508 includes a flexible diaphragm 1518 that moves in response to pressure waves in the fluid-filled lumen 1516. In accordance with the received pressure waves, the pressure sensor 1508 generates electrical signals that are transmitted to the device 100 (not shown) via one or more electrical leads 1520. As discussed above, the device 100 may then be configured to provide this pressure information to an external device or to provide appropriate therapy to the patient in response to the pressure signals.

The lead 1500 also may include one or more electrodes as discussed herein. For example a ring electrode 1522 may be located between the membranes 1502 and 1504 for unipolar pacing of the septum. One or more electrical conductors 1524 connect the electrode 1522 with the device 100. In some embodiments a membrane may be constructed of a conducting polymer. In this case, an electrical conductor (not shown) connected to the membrane may provide electrical signals from the device 100 (not shown) for pacing the septum.

Figure 16:
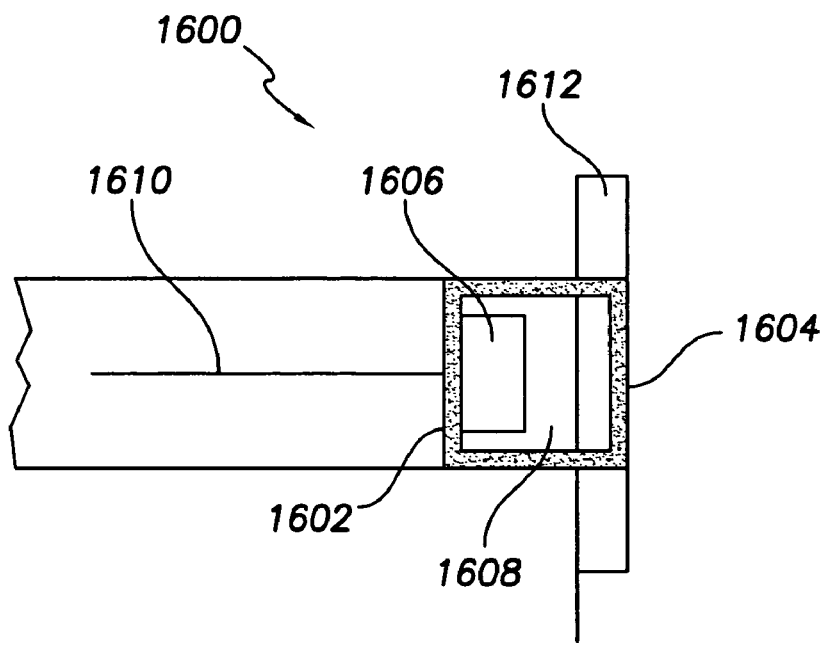
FIG. 16 is a simplified diagram of one embodiment of an implantable cardiac lead incorporating a membrane and a distal end sensor in accordance with the invention.

FIG. 16 depicts an alternative embodiment where a lead 1600 includes a pressure sensor 1602 mounted on its distal end. The sensor 1602 includes a flexible diaphragm 1604 on one end and a chip 1606 (e.g., a piezoelectric element). Pressure waves from the flexible diaphragm 1604 are transferred to the chip 1606 via a fluid-filled chamber 1608 in the sensor 1602. In accordance with the received pressure waves, the pressure sensor 1602 generates electrical signals that are transmitted to the device 100 (not shown) via one or more electrical leads 1610.

In some embodiments, an attachment structure 1612 is attached to the lead 1600 around the sensor 1602. For example, a flexible membrane, tines or other structures may be mounted on the periphery of the sensor 1602.

Figure 17:
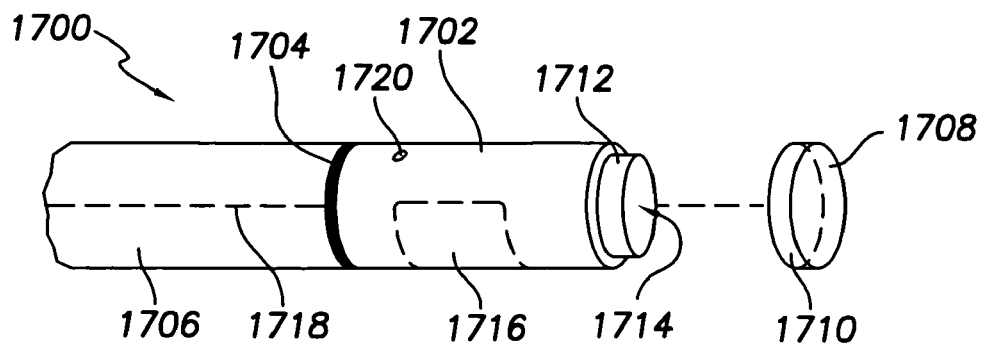
FIG. 17 is a simplified diagram of one embodiment of an implantable cardiac lead incorporating a distal end sensor in accordance with the invention.

FIG. 17 depicts one embodiment of a sensor mounted on the distal end of a lead 1700. In this example, a sensor 1702 is attached to an end 1704 of a lead body 1706. Typically, the sensor 1702 and the lead body 1706 would have the same diameter. Thus, they may be configured in a co-circumferential orientation. The sensor 1702 may be attached to the lead body 1704 by a variety of techniques including, for example, laser welding and adhesive attachment (e.g., using an epoxy).

The sensor includes a flexible diaphragm 1708 at its distal end. The sensor case and flexible diaphragm are shown in an exploded view to illustrate one technique for attaching the flexible diaphragm 1708 to the sensor case. Specifically, the flexible diaphragm 1708 may be formed with a lip that is placed over a seat provided on the end of the sensor case. Thus, an inside surface 1710 of the lip may, for example, be adhered to an outside surface 1712 of the seat. The lip of the flexible diaphragm 1708 may be attached to the seat of the sensor body using a variety of techniques including, for example, laser welding and adhesive attachment (e.g., using an epoxy). The configuration of FIG. 17 may provide an advantageous form of attachment in that welding may be avoided on the end portion of the flexible diaphragm. Thus, stresses and/or damage may be avoided on the portion of the diaphragm that flexes in response to pressure waves.

In general, various aspects of the sensor may be constructed using known materials and techniques. For example, the sensor case may be constructed of a variety of materials including, for example, titanium or another biocompatible metal. The sensor may include a pressure-to-electrical transducer 1716 such as a piezoelectric chip. One or more electrical conductors 1718 are routed out the proximal end of the sensor 1702 through the lead 1700 to connect the sensor 1702 to the device 100 (not shown).

The case interior 1714 may be filled with a biocompatible fluid or gel such as, for example, silicone oil. A port 1720 may be provided in the sensor case to facilitate filling the interior 1714 with fluid and for removing bubbles from the fluid. A plug mechanism such as a screw may be used to close the port 1720.

Figure 18:
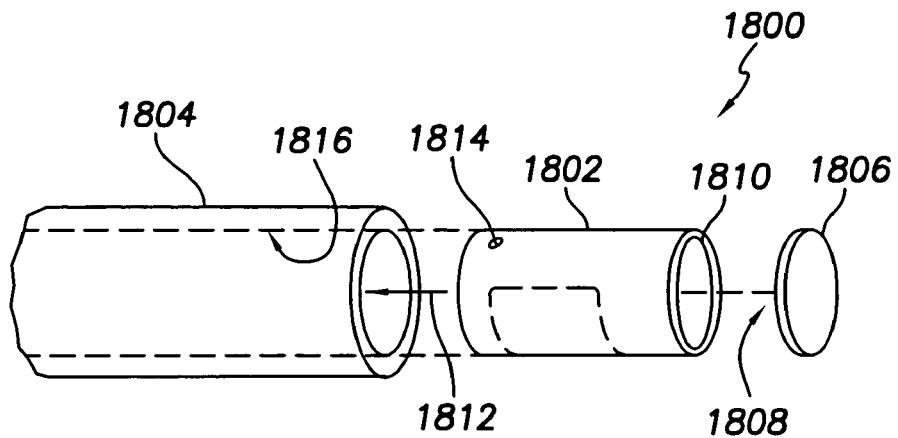
FIG. 18 is a simplified diagram of one embodiment of an implantable cardiac lead incorporating a distal end sensor in accordance with the invention.

FIG. 18 depicts an embodiment of a lead 1800 where a sensor 1802 is inserted into a distal end of a lead body 1804. The sensor 1802 includes a flexible diaphragm 1806 on its distal end. The lead body 1804 and sensor 1802 are shown in an exploded view to illustrate how these components may be assembled.

In the embodiment of FIG. 18, the flexible membrane 1806 is attached to the end of the sensor case. For example, a surface 1808 on the outer rim of the proximal side of the flexible diaphragm 1806 may be affixed to an outer rim surface 1810 of the sensor case. The surfaces 1808 and 1810 may be affixed using a variety of techniques including, for example, laser welding and adhesive attachment (e.g., using an epoxy).

The sensor 1802 is inserted into the lead body 1804 as indicated by the arrow 1812. In this case, an outside surface 1814 of the sensor 1802 may be affixed to an inside surface 1816 of the lead body 1804. Typically, sensor 1802 will be fully inserted into the lead body 1804. Thus, the distal ends of the lead body 1804 and the sensor 1802 (e.g., the flexible diaphragm 1806) may be aligned. In this case the attachment structures (not shown) may be attached to or built into the lead body 1804.

Figure 19:
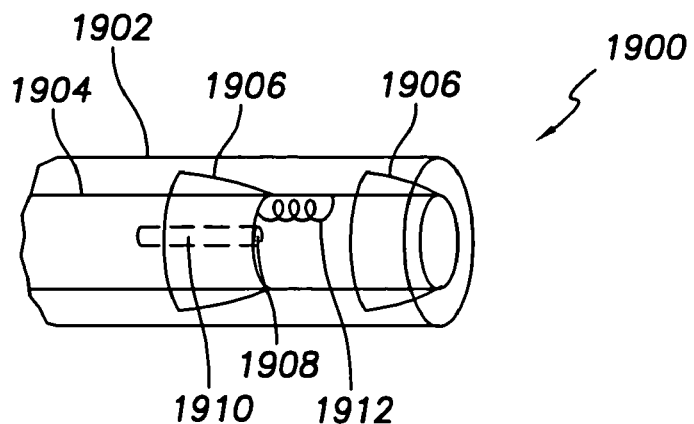
FIG. 19 is a simplified diagram of one embodiment of an implantable cardiac lead incorporating membranes and a sheath in accordance with the invention.

FIG. 19 illustrates the distal end of an embodiment of a lead 1900 that includes a sheath 1902 that slides over a lead body 1904. The sheath 1902 may be used, for example, to cover flexible membranes 1906 attached to the lead when the lead is being implanted. This may improve the maneuverability of the lead and/or simplify the implantation procedure. The sheath 1902 may be removed from the lead 1900 once the flexible membranes 1906 are properly positioned.

FIG. 19 also illustrates an embodiment where a membrane 1906 is slidably mounted to the lead 1900. As described above, a membrane 1906 may slide on the outside of the body of the lead 1900 where the travel of the membrane is restricted by a tongue 1908 and groove 1910 structure. In addition, a biasing member 1912 such as a spring may bias a membrane 1906 to automatically adjust to various septal wall thicknesses.

Figure 20:
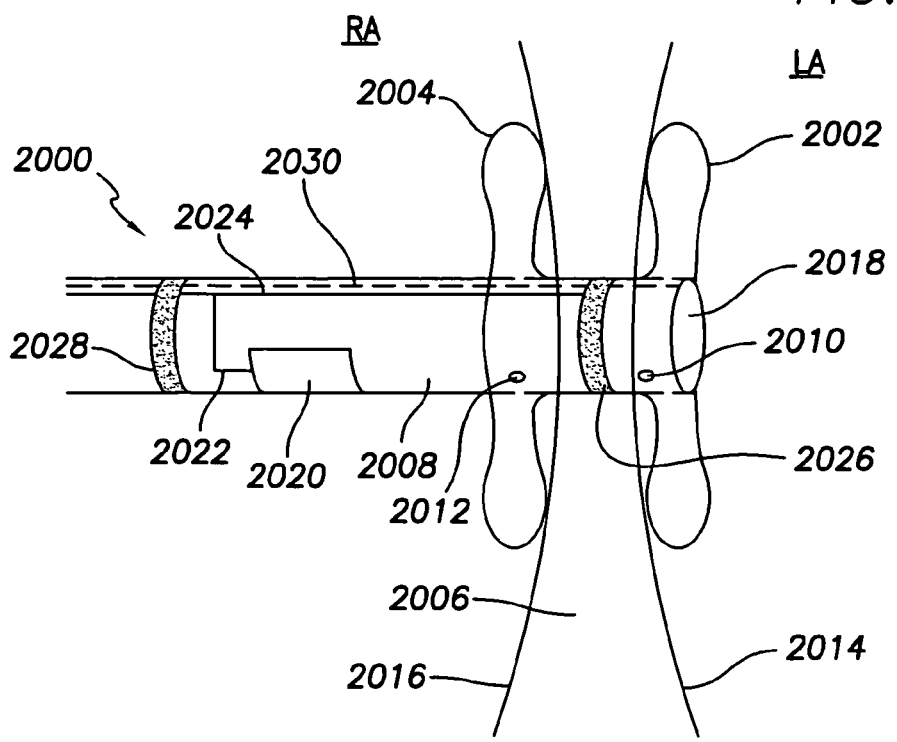
FIG. 20 is a simplified diagram of one embodiment of an implantable cardiac lead incorporating balloons in accordance with the invention.
Figure 21:
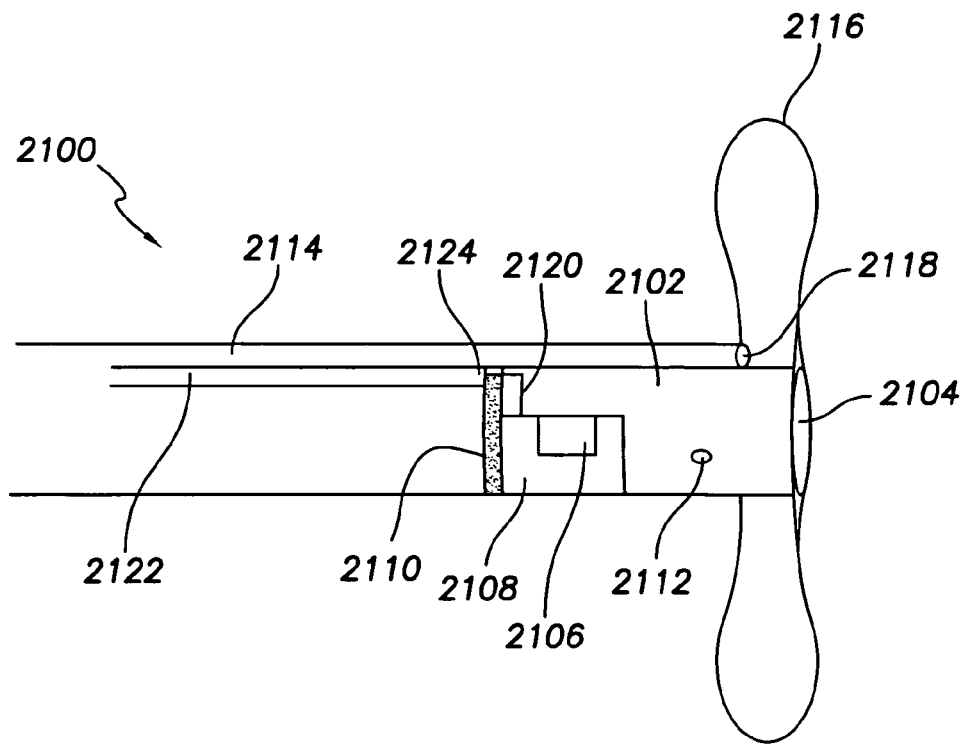
FIG. 21 is a simplified diagram of one embodiment of an implantable cardiac lead incorporating a balloon in accordance with the invention.
Figure 22:
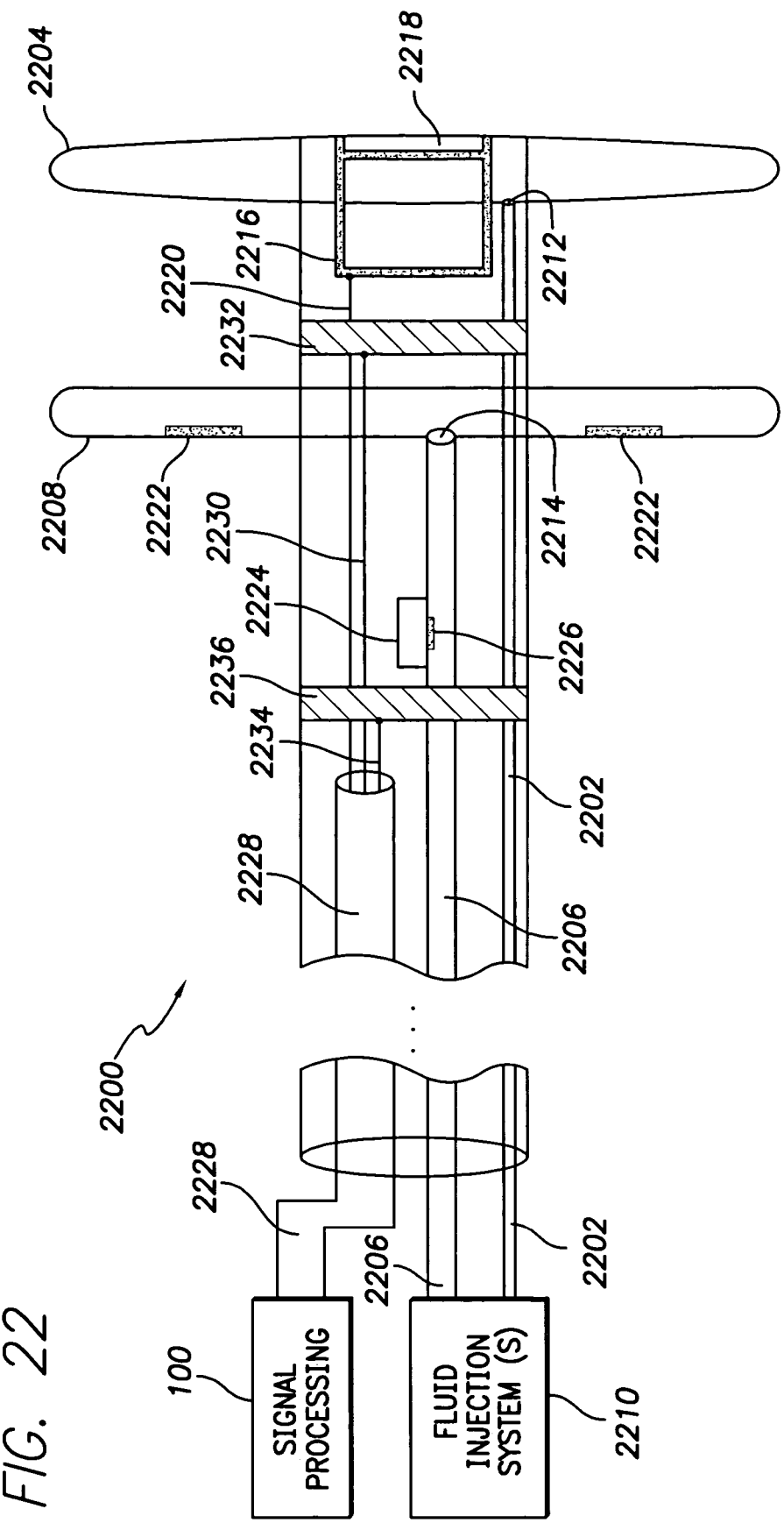
FIG. 22 is a simplified diagram of one embodiment of an implantable cardiac lead incorporating balloons in accordance with the invention.

Referring now to FIGS. 20-22, various embodiments of leads that incorporate one or more inflatable membrane or balloon-like attachment structures (hereafter referred to as "balloons" for convenience) will be discussed. The distal end of a lead including such a balloon may be implanted in the left side of the heart (e.g., the left atrium) as discussed above in conjunction with FIG. 14. During implantation, the balloon typically would be deflated. After the balloon is maneuvered to a desired location (e.g., against a septal wall in the left atrium), the balloon is inflated and serves to fix the lead to the septum. The distal end of the lead may include a pressure sensor or it may include a flexible diaphragm that is used to couple pressure waves from the left side of the heart to a sensor in the lead via a lumen filled with a fluid. Thus, the lead may be used to accurately measure pressure in the left side of the heart.

FIG. 20 depicts the distal end of one embodiment of a lead 2000 that incorporates two balloons 2002 and 2004. The balloon 2002 is located on the distal end of the lead 2000 and is implanted on the left side of a septal wall 2006 (e.g., in the left atrium "LA"). The second balloon 2004 is located on the lead 2000 so as to be located on the right side of the septum 2006 when the lead 2000 is implanted. By properly sizing and positioning the balloons 2002 and 2004, then controlling the expansion of the balloons 2002 and 2004, the expanded balloons 2002 and 2004 may be firmly pressed against each side of the septum 2006 to securely fix the lead 2000 to the septum.

In the embodiment of FIG. 20 each balloon is in fluid communication with a fluid-filled chamber 2008 (e.g., a lumen) in the lead 2000. For example, the balloons 2002 and 2004 may include ports 2010 and 2012, respectively that provide paths for fluid flow between the balloons 2002 and 2004 and the chamber 2008.

The chamber 2008 may be accessible at or near the proximal end of the lead 2000. An inflation device (not shown) may be attached to the proximal end of the chamber 2008 to inflate the balloons 2002 and 2004 after they are positioned across the septum 2006.

Once inflated, the balloons 2002 and 2004 serve to fix the lead in place. For example, the balloon 2002 may be positioned against a septal wall 2014 and may prevent the lead 2000 from being pulled in a proximal direction through the septum 2006. In addition, the balloon 2004 may be positioned against a septal wall 2016 and may prevent the lead 2000 from being extended further into the left side of the heart. Moreover, as the body may quickly build up the intima over the balloons 2002 and 2004, the balloons 2002 and 2004 may become firmly fixed to the septal walls 2014 and 2016, respectively, in a relatively short period of time.

The balloons 2002 and 2004 may be constructed to lie relatively flat against the septal walls 2014 and 2016 and to have a relatively low profile. Thus, the balloons 2002 and 2004 may serve to securely attach the lead 2000 to the septum 2006 without encroaching too far into the left side of the heart. Due to this low profile the likelihood of blood clots breaking loose may be significantly reduced as compared to leads that protrude relatively deeply into the left side of the heart.

Once the lead 2000 is secured in place, a flexible diaphragm 2018 located at the distal end of the lead 2000 may be used to detect pressure in the left side of the heart. For example, pressure waves from the left side of the heart will be transmitted by the flexible diaphragm 2018 to the adjacent fluid-filled chamber 2008. The fluid in the chamber 2008 transmits the pressure waves from the flexile membrane 2018 to a sensor located at a location along the length of the lead 2000 (e.g., sensor 2020) or located in the device 100 (sensor not shown).

In some embodiments the flexible diaphragm 2018 may be part of the balloon 2002. In other embodiments, however, the flexible diaphragm 2018 may be a separate component of the lead 2000. Examples of various configurations are discussed below.

In accordance with the received pressure waves, the pressure sensor 2020 generates electrical signals that are transmitted to the device 100 (not shown) via one or more electrical conductors 2022. The electrical conductors 2022 may be routed through the lead 2000 via a lumen 2024. As discussed above, the device 100 may then be configured to provide this pressure information to an external device or to provide appropriate therapy to the patient in response to the pressure signals.

The lead 2000 also may include one or more electrodes that may be used to apply stimulation signals to the septum or sense signals in the area of the septum. For example, a first ring electrode 2026 may be located between the balloons 2002 and 2004 for unipolar pacing of the septum 2006. In addition, a second ring electrode 2028 may be incorporated into the lead 2000 proximal to the second balloon 2004 to provide bipolar pacing or sensing in conjunction with the electrode 2026. The electrical connections between the electrodes 2026 and 2028 and the device 100 may be routed through the lumen 2024 as represented by the dashed line 2030.

In the embodiment of FIG. 20 the balloons 2002 and 2004 may be inflated by forcing fluid into the chamber 2008. Under pressure, the fluid is forced through ports 2010 and 2012 into the uninflated balloons 2002 and 2004. Thus, in this embodiment, the balloons are filled with the same fluid that is used to transmit pressure waves from the flexible diaphragm 2018 to the sensor 2020.

FIG. 21 illustrates an alternative embodiment of a lead 2100 that uses separate fluid paths for pressure wave transmission and balloon inflation. Fluid in a sealed chamber 2102 is used to transmit pressure waves from a flexible diaphragm 2104 at the distal end of the lead 2100 to a flexible diaphragm 2106 of a sensor 2108. A wall 2110 may be used to seal the chamber 2102 from other areas within the lead 2100.

The lead 2100 may include a port 2112 for filling the chamber 2102. As discussed above, once the chamber 2102 has been filled and all bubbles removed from the fluid, the port 2112 may be sealed using, for example, a screw (not shown).

A separate lumen 2114 is used to fill a balloon 2116. Fluid from the lumen 2114 is forced through a port 2118 into the interior of the balloon 2116. In this case the shape of the balloon 2116 may take the form of a doughnut since the balloon 2116 surrounds the circumference of the chamber 2102.

One or more electrical conductors 2120 from the sensor may be routed to the device 100 (not shown) via another lumen 2122. In this case, an entrance port 2124 to the lumen may be sealed to prevent fluid flow to or from the lumen 2122 and the chamber 2102.

In the embodiment of FIG. 20 the balloons 2002 and 2004 are in fluid connection with a common fluid carrying chamber. As a result, both balloons 2002 and 2004 are inflated at the same time after they are positioned at the desired location.

In some embodiments separate lumens may be used to inflate two or more balloons. For example, FIG. 22 depicts a distal portion of one embodiment of a lead 2200 where a first lumen 2202 is in fluid communication with a first balloon 2204 and a second lumen 2206 is in fluid communication with a second balloon 2208. Inflation/deflation of each of the balloons 2204 and 2208 may then be individually controlled by one or more fluid injection systems 2210 connected to the proximal ends of the lumens 2202 and 2206. That is, the fluid injection system(s) 2210 may cause fluid to flow between the lumens 2202 and 2206 and the balloons 2204 and 2208 via ports 2212 and 2214, respectively.

FIG. 22 illustrates an embodiment where a sensor 2216 may be located at the end of the lead 2200. The sensor 2216 may take a form described, for example, in conjunction with FIGS. 16-18. Thus, pressure waves in the left side of the heart cause movement of a flexible diaphragm 2218 in the sensor 2216 which causes the sensor to transmit corresponding electrical signals via one or more electrical conductors 2220.

In some embodiments, the second balloon 2208 may incorporate one or more flexible diaphragms 2222 to detect pressure in the right side of the heart. To this end the flexible diaphragm 2222 and a flexible diaphragm 2226 of a second sensor 2224 may be in fluid communication with a common fluid. For example, as shown in FIG. 22, the fluid used to inflate the balloon 2208 may be used to carry pressure waves from the flexible diaphragm 2222 to the sensor 2224.

FIG. 22 also illustrates that a separate lumen 2228 may be used to route the electrical conductors from the components on the distal end of the lead 2200 to the device 100 that provides signal processing. For example, in some embodiments the signal processing may generate stimulation signals that are transmitted over an electrical conductor 2230 to a ring electrode 2232. In some embodiments the signal processing may receive bipolar signals via a conductor 2234 from an electrode 2236 and the conductor 2230 from the electrode 2232 to sense electrical activity in the vicinity of the distal end of the lead 2200.

In some embodiments the deflated balloons may be formed to lie relatively flat against the intra cardiac lead. As a result, the lead may be easily maneuvered though the body and the access tunnel. In some embodiments a moveable sheath may be used to encase the balloons as described above in conjunction with FIG. 19. The sheath may be used to ensure that the balloons do not interfere with the maneuvering of a lead. In this case, the sheath may be removed from the lead once the balloons are properly positioned.

It should be appreciated that a variety of lead structures and configurations may be used in accordance with the teachings herein. For example, a lead body may be constructed using a variety of materials as discussed above. In addition, the balloons may be formed in various shapes and constructed of various materials. For example, the balloons may be constructed using biocompatible material such as silicone rubber or polyurethane.

A variety of fluids may be used to inflate the balloons and/or transmit pressure waves. For example, the fluid may consist of a biocompatible liquid such as water, saline or silicone oil. In some applications, however, the liquid needs to be compatible with gas sterilization procedures that may be used to sterilize the lead.

Figure 23:
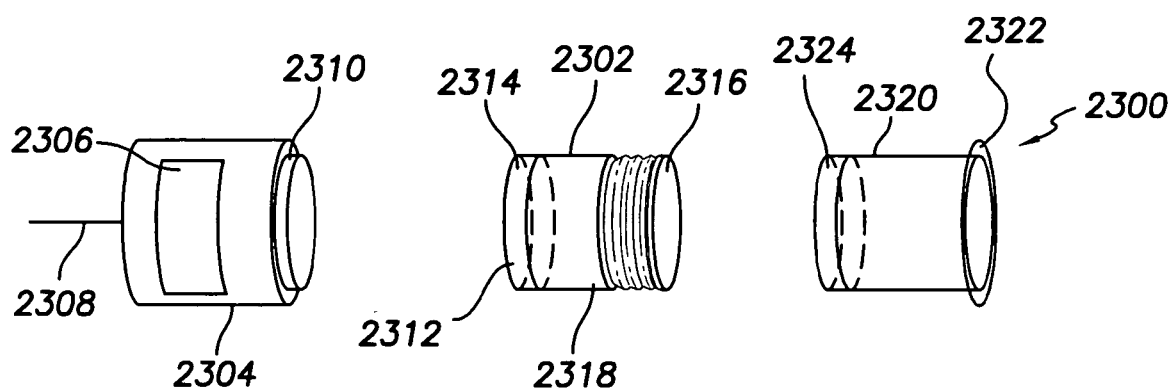
FIG. 23 is a simplified diagram of one embodiment of a sensor incorporating a bellow in accordance with the invention.
Figure 24:
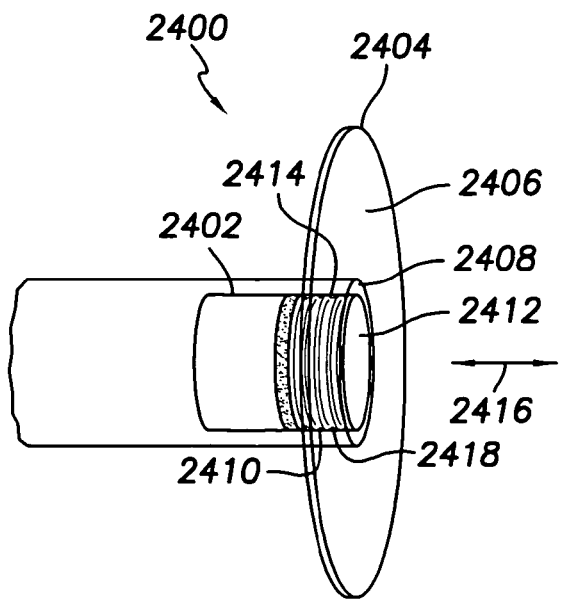
FIG. 24 is a simplified diagram of one embodiment of an implantable cardiac lead incorporating a sensor with a bellow in accordance with the invention.

FIGS. 23 and 24 illustrate an alternative embodiment of a sensor that incorporates a bellow for sensing pressure changes in the left side of the heart. Such a configuration typically would be used in embodiments where the sensor is located at the distal end of a lead.

FIG. 23 depicts an exploded view of one embodiment of a sensor 2300 incorporating a flexible bellow 2302. A main sensor body 2304 incorporates a pressure-to-electrical transducer 2306 that generates electrical signals provided to an electrical conductor 2308.

The main sensor body 2304 also includes a seat 2310 adapted to receive a base portion 2312 of the bellow 2302. An inside surface 2314 of the base portion 2312 may, for example, be adhered to an outside surface of the seat 2310 using a variety of techniques including, for example, laser welding and adhesive attachment (e.g., using an epoxy).

The distal end of the bellow comprises a wall or end piece 2316 that forms the distal end of the sensor assembly 2300. The interior 2318 of the bellow and the main body 2304 may then be filled with a non-compressible fluid.

In some embodiments, the sensor may include a bellow cover 2320. The bellow cover 2320 may facilitate attaching the sensor 2300 to a lead. For example, an attachment structure such as tines may be affixed to the outside of the bellow cover 2320. In addition, the bellow cover 2320 may include a lip 2322 to which an attachment structure such as a flexible membrane or balloon may be attached.

A base portion of the bellow cover 2320 may be adapted to be affixed to the base portion 2312 of the bellow 2302. An inside surface 2324 of the base portion of the bellow cover 2320 may, for example, be adhered to an outside surface of the base 2312 using a variety of techniques including, for example, laser welding and adhesive attachment (e.g., using an epoxy).

FIG. 24 illustrates the distal end of one embodiment of a lead 2400 that incorporates a bellow-based sensor 2402. The sensor 2402 and an attachment structure 2404 such as a membrane or a balloon are mounted on the distal end of the lead 2400.

A portion of a distal surface 2406 of the attachment structure 2404 may be affixed to a lip 2408 of a bellow cover 2410 on the sensor 2402. This fixation may be accomplished using a variety of techniques including, for example, laser welding and adhesive attachment (e.g., using an epoxy).

In operation, changes in pressure in the left side of the heart will cause a distal surface 2412 of a bellow 2414 in the sensor 2402 to move. In general, the bellow 2414 may expand and contract in the direction of the arrows 2416.

Here, provisions may be taken to prevent blood from the left side of the heart from flowing into a space 2418 between the bellow 2414 and the bellow cover 2410. For example, a thin flexible diaphragm (e.g., made of silicone) may attached over the surface 2406 including the surface 2412 of the bellow to prevent ingression of blood into the space 2418.

Referring now to FIGS. 25-28 various embodiments of leads that incorporate circumferential tine attachment structures will be discussed. In some embodiments the circumferential tines take the form of spiral or spiral-like protrusions (hereafter referred to as "spirals" for convenience). Typically, this type of lead includes a sensor on its distal end such that the sensor may be positioned in the left side of the heart when the lead is implanted. In this way, the lead may be used to monitor pressure in the left side of the heart (e.g., the left atrium).

Figure 25:
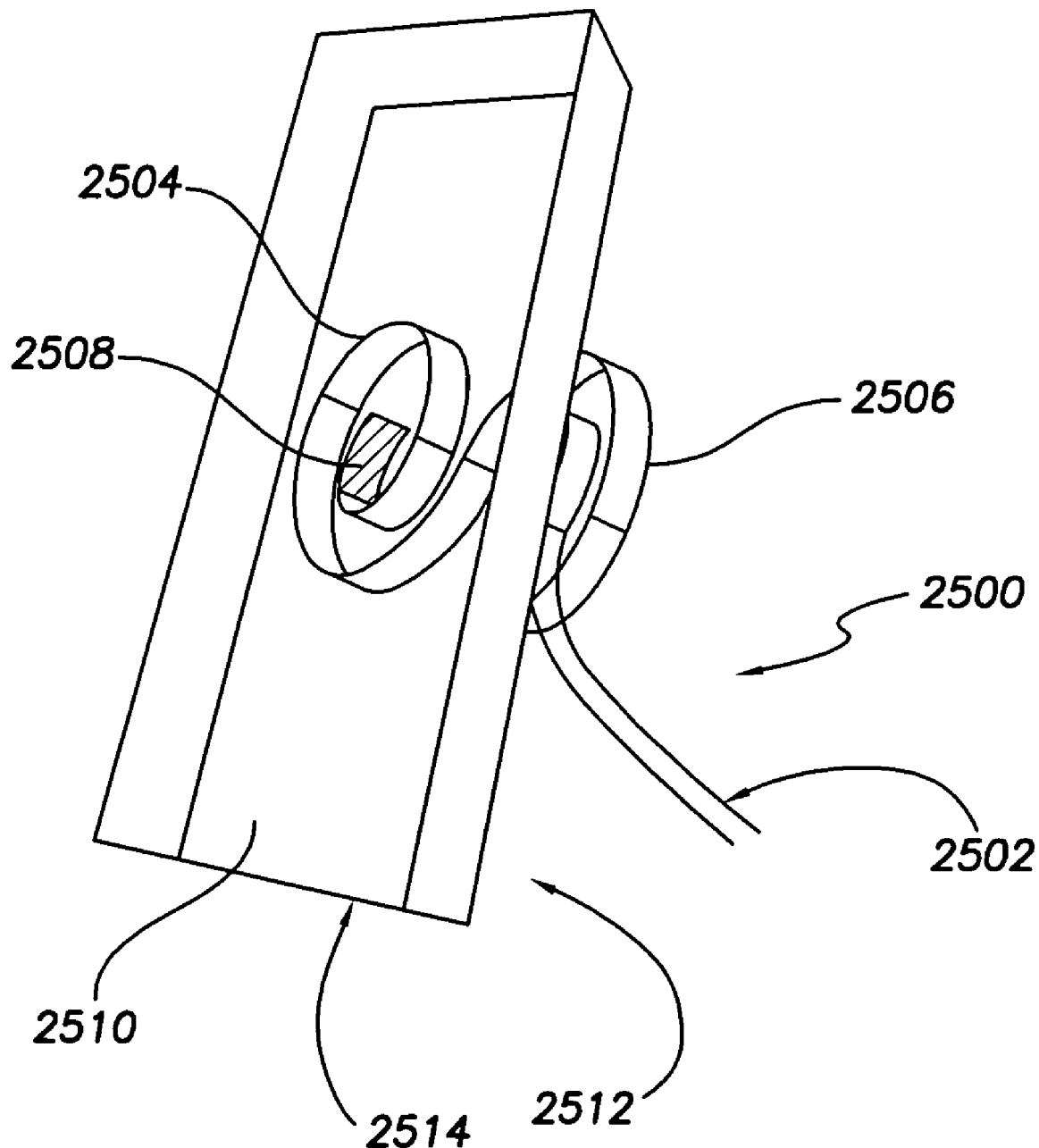
FIG. 25 is a simplified diagram of one embodiment of an implantable cardiac lead incorporating involuted spirals in accordance with the invention.

FIG. 25 illustrates the distal portion of one embodiment of a lead 2500 incorporating two oppositely oriented involuted spiral attachment structures 2504 and 2506. Before implantation, the involuted spiral portions 2504 and 2506 of the lead 2500 are maintained in a relatively straight configuration within the distal portion of a lead body 2502.

In some embodiments the involuted spirals contained within the lead 2500 and are held relatively straight by a tensile member such as a stylet (not shown) in the lead 2500. The lead 2500 may thus be maneuvered to and through the septum 2514 using a stylet as discussed above. After the distal portion of the lead 2500 is inserted into the left side of the heart, the stylet may be retracted to allow the spiral 2504 to unwind onto the septal wall 2510. The second spiral 2506 may then be unwound onto the septal wall 2512 by further retraction of the stylet.

Each spiral 2504 and 2506 is formed so that it lies relatively flat against its respective septal wall 2510 and 2512. In this way, the lead may be firmly attached to the septum 2514 yet have a relatively low profile in the left side of the heart.

In some embodiments, a pressure sensor 2508 may be incorporated in the spiral 2504. In this case, the pressure sensor 2508 may be positioned against the septal wall 2510 thereby providing a relatively low profile sensor in the left side of the heart. Accordingly, the lead 2500 may be used to provide relatively safe and accurate pressure measurements from the left side of the heart (e.g., the left atrium).

As FIG. 25 illustrates the two involuted spirals 2504 and 2506 may be configured so that one turns in a clockwise direction and the other turns in a counterclockwise direction. This configuration provides relatively stabile mechanism for securely locking the lead 2500 to the septum 2514.

In some applications, the use of involuted spirals instead of standard spirals may provide a closer fit against the septal walls 2510 and 2512. It should be appreciated, however, that a variety of spiral and other curved protrusions may be used in accordance with the teachings herein.

Figure 26:
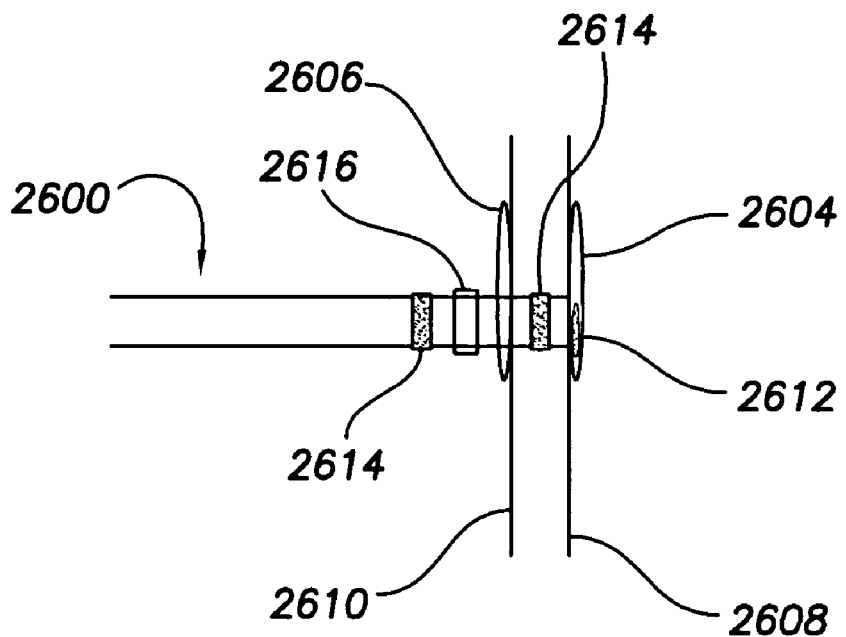
FIG. 26 is a simplified diagram of a side view of one embodiment of an implantable cardiac lead incorporating involuted spirals in accordance with the invention.

FIG. 26 is an example of a side view of a lead 2600 that shows how a spiral 2604 and a sensor 2612 may lie relatively flat against a septal wall 2608. Similarly, a spiral 2606 lies relatively flat against a septal wall 2610.

FIG. 26 also illustrates that the lead 2600 may include one or more electrodes 2614 and other sensors 2616. The construction and operation of these components may be similar to the construction and operation of other electrodes and sensors discussed herein.

Figure 27:
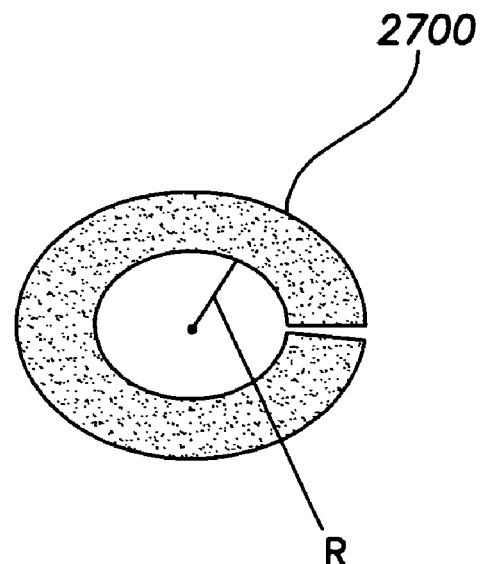
FIG. 27 is a simplified diagram of dimensions in one embodiment of an implantable cardiac lead incorporating involuted spirals in accordance with the invention.

FIG. 27 illustrates that in some embodiments the radius R of a spiral 2600 that includes a pressure sensor must be equal to or greater than the length of the pressure sensor. In this configuration all of the turns of the spiral may easily unwind one around the other.

Figure 28A:
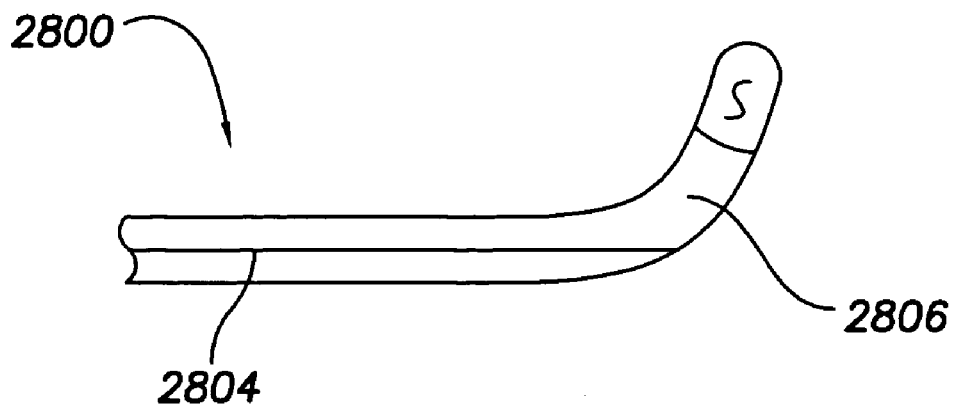
FIGS. 28A and 28B is a simplified diagram of one embodiment of an implantable cardiac lead incorporating involuted spirals and a stylet in accordance with the invention.
Figure 28B:
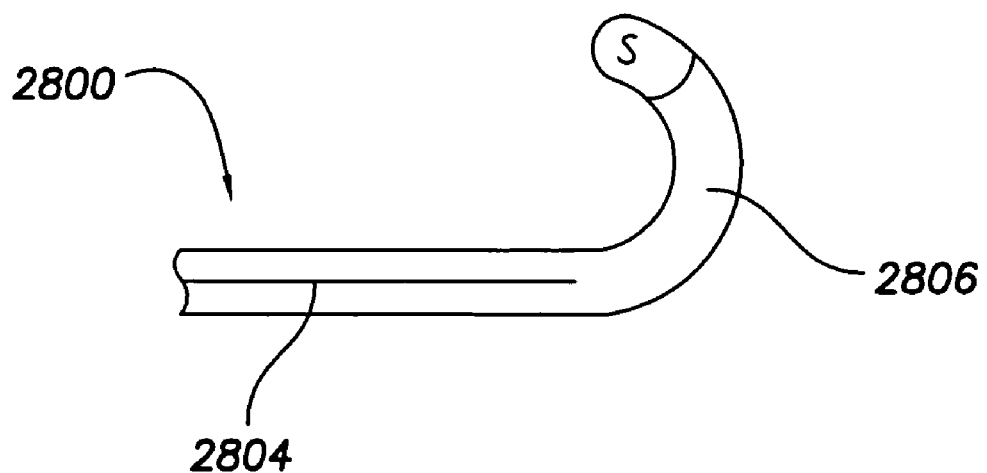

FIGS. 28A and 28B illustrate how the retraction of a stylet 2804 in a lead 2800 may cause the distal end of the lead 2806 to return to the spiral shape. In some embodiments separate removable stylets may be used to straighten each involuted spiral for the initial implantation procedure. Alternatively the lead may be configured so that a single stylet is used to straighten both spirals.

The use of the stylet 2804 may also enable removal of the lead 2800 after it has been implanted. For example, by reinserting the stylet 2804 into the lead 2800 the spirals may be straightened out thereby facilitating removal of the lead from the septum.

Figure 29:
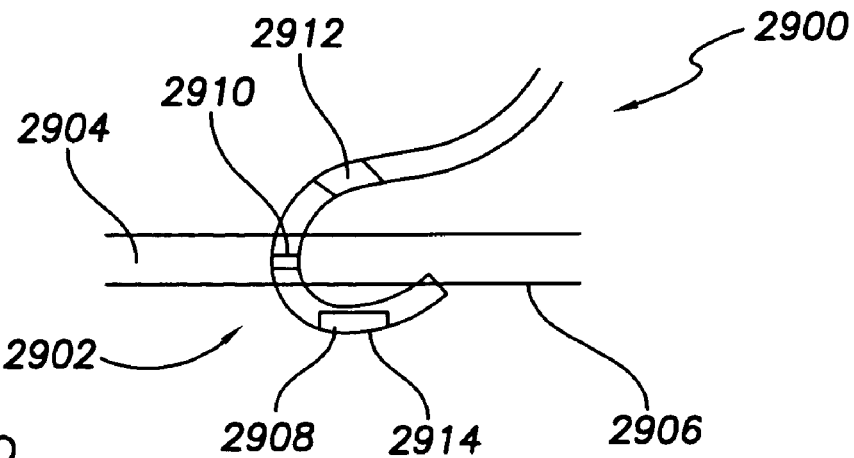
FIG. 29 is a simplified diagram of one embodiment of an implantable cardiac lead incorporating a J-lead structure in accordance with the invention.
Figure 30:
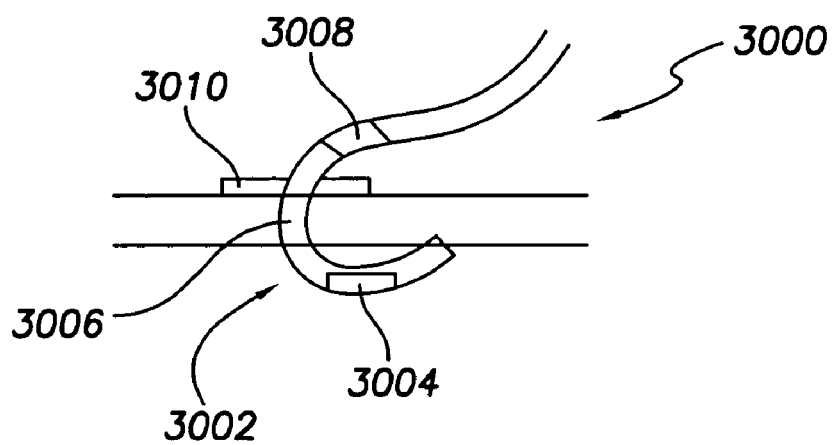
FIG. 30 is a simplified diagram of one embodiment of an implantable cardiac lead incorporating a J-lead structure and an attachment structure in accordance with the invention.
Figure 31:
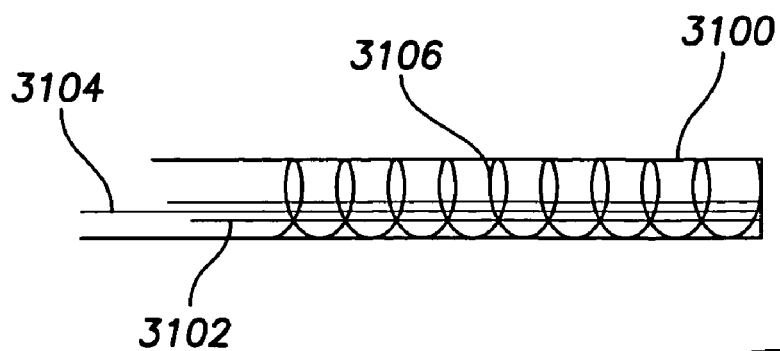
FIG. 31 is a simplified diagram of one embodiment of an implantable cardiac lead incorporating a J-lead structure and a stylet in accordance with the invention.

FIGS. 29-31 illustrate the distal ends of several embodiments of leads that incorporate attachment structures that take the form of a J-lead. A J-lead structure on the distal ends of the leads may be used to provide a relatively secure and low profile attachment to a septal wall on the left side of the heart. In addition, the J-lead portion may accommodate a sensor, thereby enabling accurate pressure measurements in the left side of the heart.

FIG. 29 illustrates the distal end of one embodiment of a lead 2900 incorporating a J-lead structure 2902. During implantation, the J-lead structure 2902 is maneuvered through a septum 2904 so that the end of the J-lead rests against a septal wall 2906 in the left side of the heart.

In some embodiments the J-lead structure incorporates a pressure sensor 2908. As FIG. 29 illustrates, with an appropriate configuration of the J-lead 2902, the sensor 2908 and the J-lead may exhibit a relatively low profile in the left side of the heart. In the embodiment of FIG. 29, the sensor 2908 may be installed in the lead 2900 such that a flexible diaphragm 2914 in the sensor forms a portion of the exterior surface of the lead 2900.

FIG. 29 also illustrates that the lead 2900 may include one or more electrodes 2910 for pacing and/or sensing in the septal area. In addition, the lead 2900 may include other pressure sensors as discussed herein. For example, a pressure sensor 2912 may be used to obtain pressure measurement in the right side of the heart.

FIG. 30 illustrates the distal end of a lead 30 where a J-lead structure 3002 include a flexible diaphragm 3004 that may be positioned in the left side of the heart. The lead 3000 also includes a fluid-filled chamber (e.g., a lumen) 3006 that is used to transmit pressure waves from the flexible diaphragm 3004 to a pressure sensor located anywhere within the lead 3000 (e.g., sensor 3008) or a pressure sensor located in the device 100 (not shown).

FIG. 30 also illustrates that the lead 3000 may incorporate one or more attachment structures 3010. For example, a tine, membrane, balloon or spiral structure as discussed herein may be used to help prevent the lead 3000 from encroaching further into the left side of the heart. In addition, as discussed herein the attachment structures 3010 may be adjustable (e.g., slidably mounted on the lead 3000).

In some embodiments the radius of the J-lead structure 3002 may be sufficiently small so that the J-lead structure 3002 may be inserted through an access tunnel in a septum. In some embodiments the J-lead structure 3002 comprises a relatively tight loop. For example, such a loop may form almost a full circle.

In some embodiments a tensile member such as a stylet (not shown) may be incorporated into the lead to substantially straighten the J-lead structure during the implantation procedure. One example of this configuration is illustrated in FIG. 31.

In FIG. 31 a lead 3100 includes a lumen 3102 which, in turn, carries a stylet 3104. When the stylet 3104 is fully inserted into the lumen 3102 the shape of the lead 3100 may be controlled by the stylet 3104. As a result, the distal end of the lead 3100 may be maneuvered to and through a septum (not shown) using the stylet 3104 as discussed above. After the distal portion of the lead 3100 is inserted into the left side of the heart, the stylet may be retracted to allow the J-lead structure to curve onto the septal wall.

In some embodiments the shape of the J-lead structure may be defined by one or more springs 3106 in the lead 3100. It should be appreciated, however, that a variety of techniques may be used to provide the desired shape for the J-lead portion of a lead.

A variety of lead structures and configurations may be used in accordance with the teachings herein. For example, a lead body may be constructed using various materials as discussed above. In addition, the spirals and J-leads may be formed in various shapes and constructed of various materials. For example, the spirals and J-leads may be constructed of biocompatible material such as Nitinol, MP35N, silicone rubber or similar polymers that may be processed into a spiral shape. An advantage of Nitinol is that it has relatively good flexibility and mechanical properties.

It should be appreciated from the above description that a variety of pressure measurements may be made using a lead constructed in accordance with the teachings herein. For example, referring to FIG. 32, pressure in the thoracic cavity relative to a chamber in the heart may be accomplished indirectly using one or more leads as described herein. As represented by block 3202, pressure between the thoracic cavity and a first chamber is initially measured. Then, as represented by block 3204, pressure between the first chamber and a second chamber is measured. Next, as represented by block 3206 the pressure between the thoracic cavity and the second chamber may be calculated by, for example, taking the difference between the two measurements from blocks 3202 and 3204. Based on this relative thoracic pressure calculation, an appropriate action (e.g., notification or application of therapy) may be performed as discussed herein (block 3208).

Figure 32:
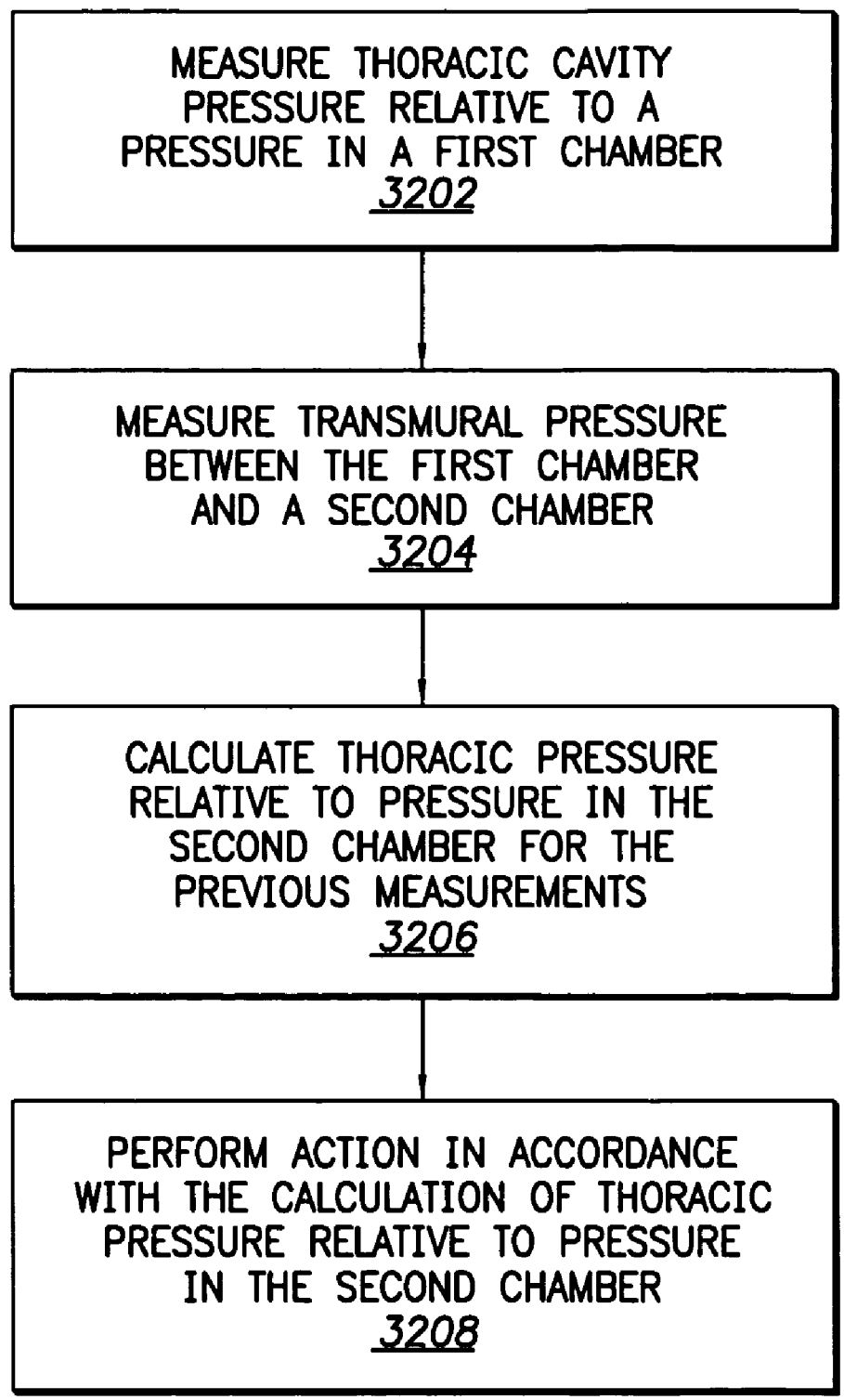
FIG. 32 is a simplified flow chart of one embodiment of pressure measurement operations that may be performed in accordance with the invention.

Four examples of relative pressure that may be calculated in accordance with FIG. 32 follow. Thoracic cavity to left atrium pressure may be calculated by measuring thoracic cavity to right atrium pressure, measuring right atrium to left atrium transmural pressure, then taking the difference between these two measured pressures. Thoracic cavity to left ventricle pressure may be calculated by measuring thoracic cavity to right ventricle pressure, measuring right ventricle to left ventricle transmural pressure, then taking the difference between these two measured pressures. Thoracic cavity to right ventricle pressure may be calculated by measuring thoracic cavity to left ventricle pressure, measuring left ventricle to right ventricle transmural pressure, then taking the difference between these two measured pressures. Thoracic cavity to right atrium pressure may be calculated by measuring thoracic cavity to left atrium pressure, measuring left atrium to right atrium transmural pressure, then taking the difference between these two measured pressures.

In embodiments that measure aorta pressure, pressure measurement information may be obtained for a variety of clinical applications. For example, measurement of aortic pressure may provide some measure of hypertensive status. In addition, a pressure gradient across the mitral valve (left atrium to left ventricle pressure measurement) may be obtained as well as a pressure gradient across the aortic valve (left ventricle to aorta pressure measurement).

In addition, as discussed above pressure measurements may be made relative to the pocket (e.g., can 200) in embodiments where the pressure sensor may be located in the pocket. Thus, the sensor may be vented to the pocket.

Moreover, a variety of pressure measurements may be made using only a single lead or a pair of leads. For example, a single lead incorporating a pair of trans-septal leads (one each for the atrial septum and the ventricular septum) and one or more branch leads may be used to measure LV, RV, RA, LA and thoracic pressure. Alternatively two or more leads may be configured with various pressure sensors and attachment structures to accomplish these measurements.

In view of the above, it should be understood that a lead may be constructed using various combinations and modifications of the structures and components described herein. For example, the structure and components described in a given drawing may be used in a lead described in another drawing. In addition, lead components such as sensors, electrodes, attachment structures and flexible diaphragms may be located at various locations on the lead.

In addition, the structures described herein may be implemented in a variety of ways. For example, the leads described herein may be form by attaching various components together. Also, the combinations of some of the components which are described herein as being "attached," "connected" "including," "affixed," etc., may be implemented as one or more integral components.

Figure 33:
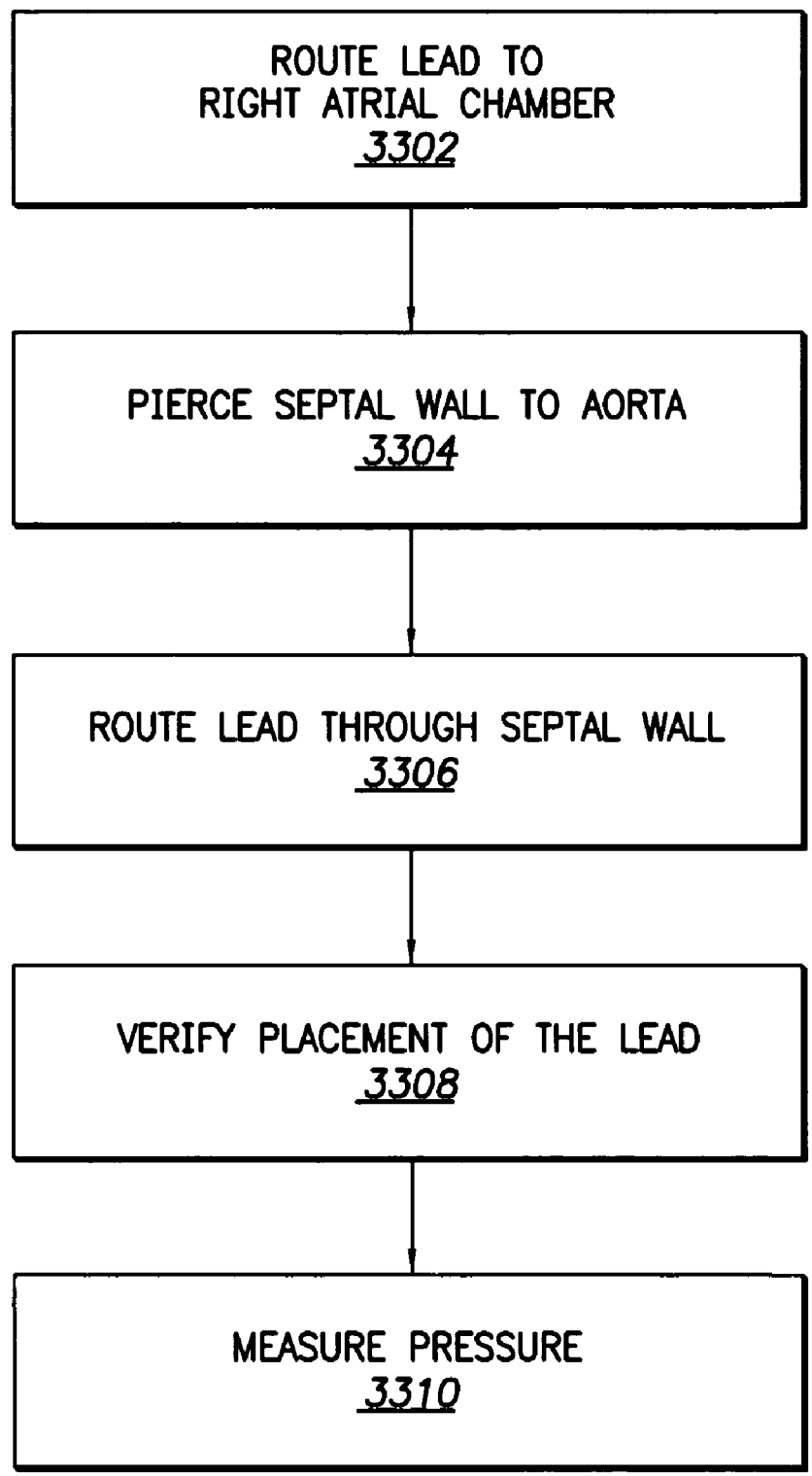
FIG. 33 is a simplified flow chart of one embodiment of pressure measurement operations that may be performed in accordance with the invention.
Figures 34A, 34B:
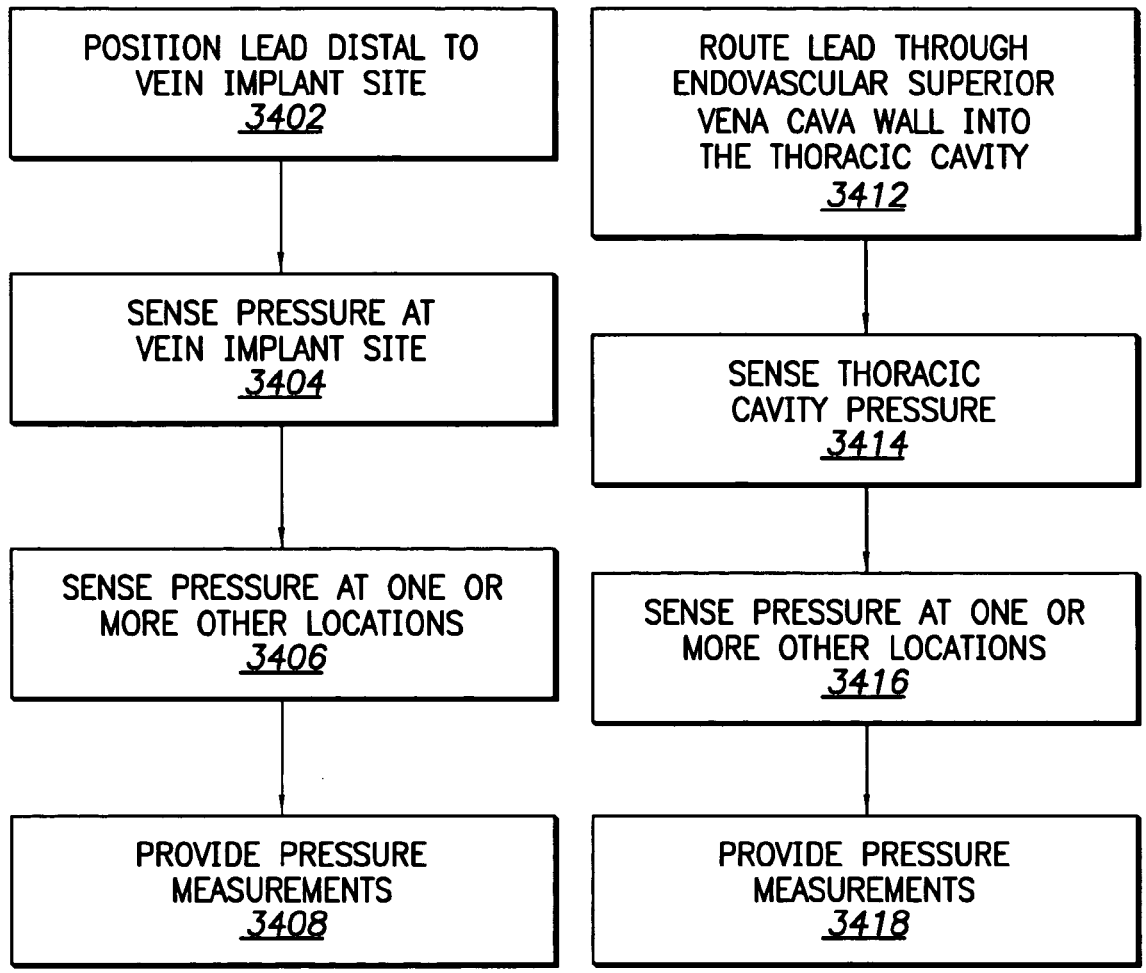
FIGS. 34A-34D are simplified flow charts of embodiments of pressure measurement operations that may be performed in accordance with the invention.
Figures 34C, 34D:
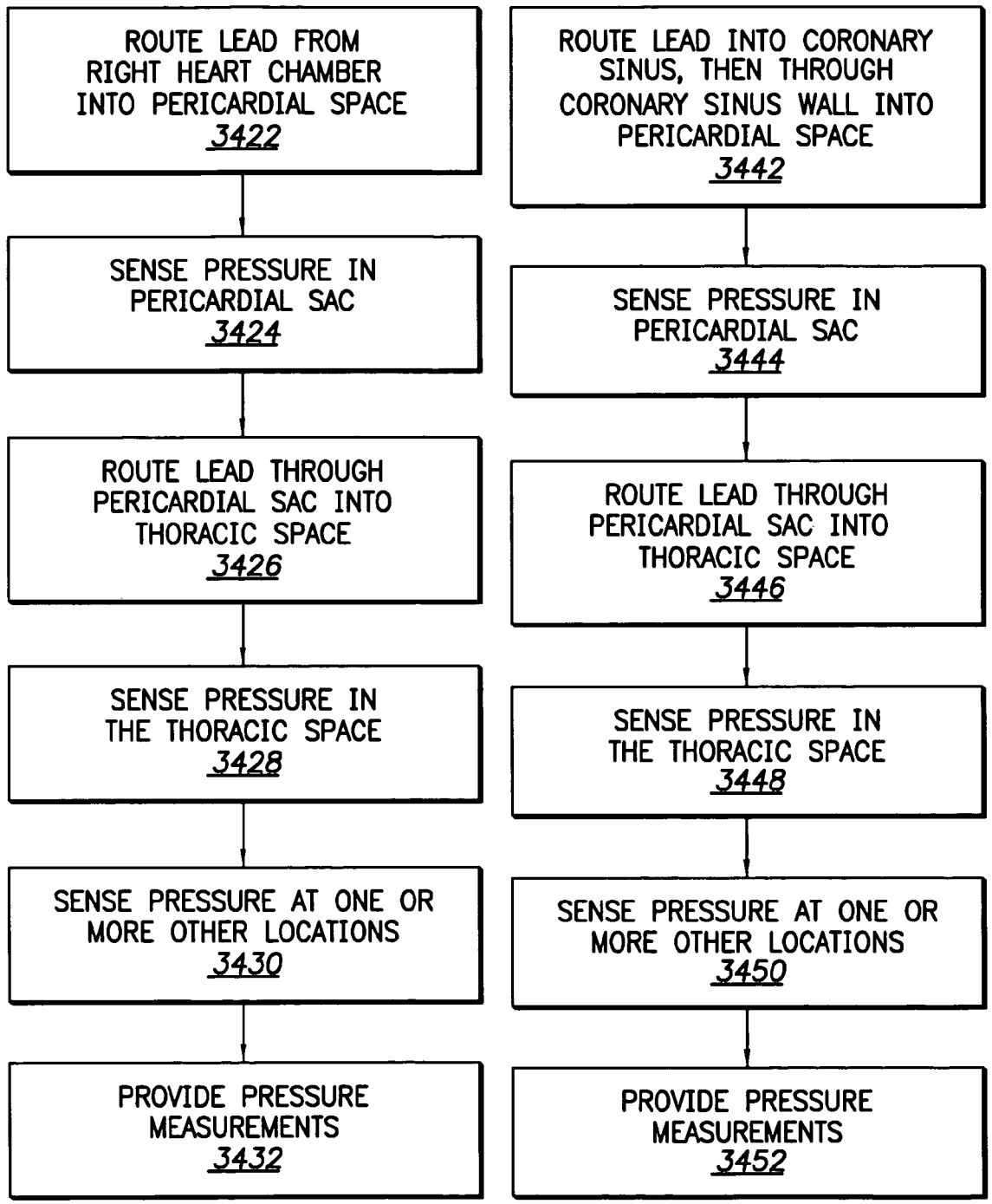

Referring to FIG. 33, in situations in which arterial pressure is to be measured, a lead may be placed through the portion of the septal wall that separates the right atrial chamber from the root of the aorta. This technique allows for ready access to arterial blood pressure using transvenous access techniques. Placement in this location may be completely analogous to placement of a lead in the left atrium through the right atrial septum. In some embodiment this technique involves routing the lead to the right atrial chamber (block 3302), piercing the septal wall that separates the right atrial chamber from the root of the aorta (block 3304) and routing the lead through the septal wall (block 3306). Blood pressure measured at the time of implant may be used to confirm placement in the aorta since aortic pressures are significantly higher than left atrial pressure (block 3308). After implantation, the desired pressure measurements may be taken (block 3310). As discussed herein these pressure measurements may be made with respect to one or more other pressure measurements.

Referring to FIGS. 34A-34D, thoracic pressure may be accessed by a variety of means. For example, in some embodiments the lead may be positioned at a location immediately distal to a subclavian or cephalic vein implant site within the rib cage (block 3402) as this location may be regarded as an intrathoracic pressure site. Typically there is little or no blood flow through the vein at this location since the vein has been tied off during the implant process. Pressure at this location (block 3404) and, optionally, one or more other locations (block 3406) may then be sensed to provide the desired direct or relative pressure measurements (block 3408).

In some embodiments a sensor may be placed in the thoracic space by going through the endovascular superior vena cava wall into the thoracic cavity (Block 3412). Pressure at this location (block 3414) and, optionally, one or more other locations (block 3416) may then be sensed to provide the desired pressure measurement (block 3418).

In some embodiments a pressure sensor may be placed through the right atrial wall or right ventricular wall into the pericardial space (block 3422). It should be noted here that the pressure in the pericardial sac may approximate intrathoracic pressure with exception of situations in which the heart is not excessively enlarged or in situations in which pericardial fluid has accumulated. This is typically caused by pathologic events leading to pericardial effusion secondary to tamponade, trauma, or inflammatory process leading to fluid ingression into the pericardial space. Thus, in some embodiments pressure may be measured in the pericardial sac (block 3424). Alternatively, if the lead with its sensor is advanced even further though the pericardial sac into the thoracic space (block 3426) thoracic pressure may be directly measured (block 3428). Pressure at either of these locations (block 3424 or 3428) and, optionally, one or more other locations (block 3430) may then be sensed to, for example, provide a desired pressure measurement (block 3432).

In some embodiments the sensor lead may be advanced into the coronary sinus, then through the coronary sinus wall into the pericardial space (block 3442). As discussed above pressure may be measured in the pericardial sac (block 3444) or, alternatively, the lead may be routed through the pericardial sac into the thoracic cavity (block 3446) to obtain thoracic pressure (block 3448). Pressure at either of these locations (block 3444 or 3448) and, optionally, one or more other locations (block 3450) may then be sensed to provide, for example, a desired pressure measurement (block 3452).

Figure 35:
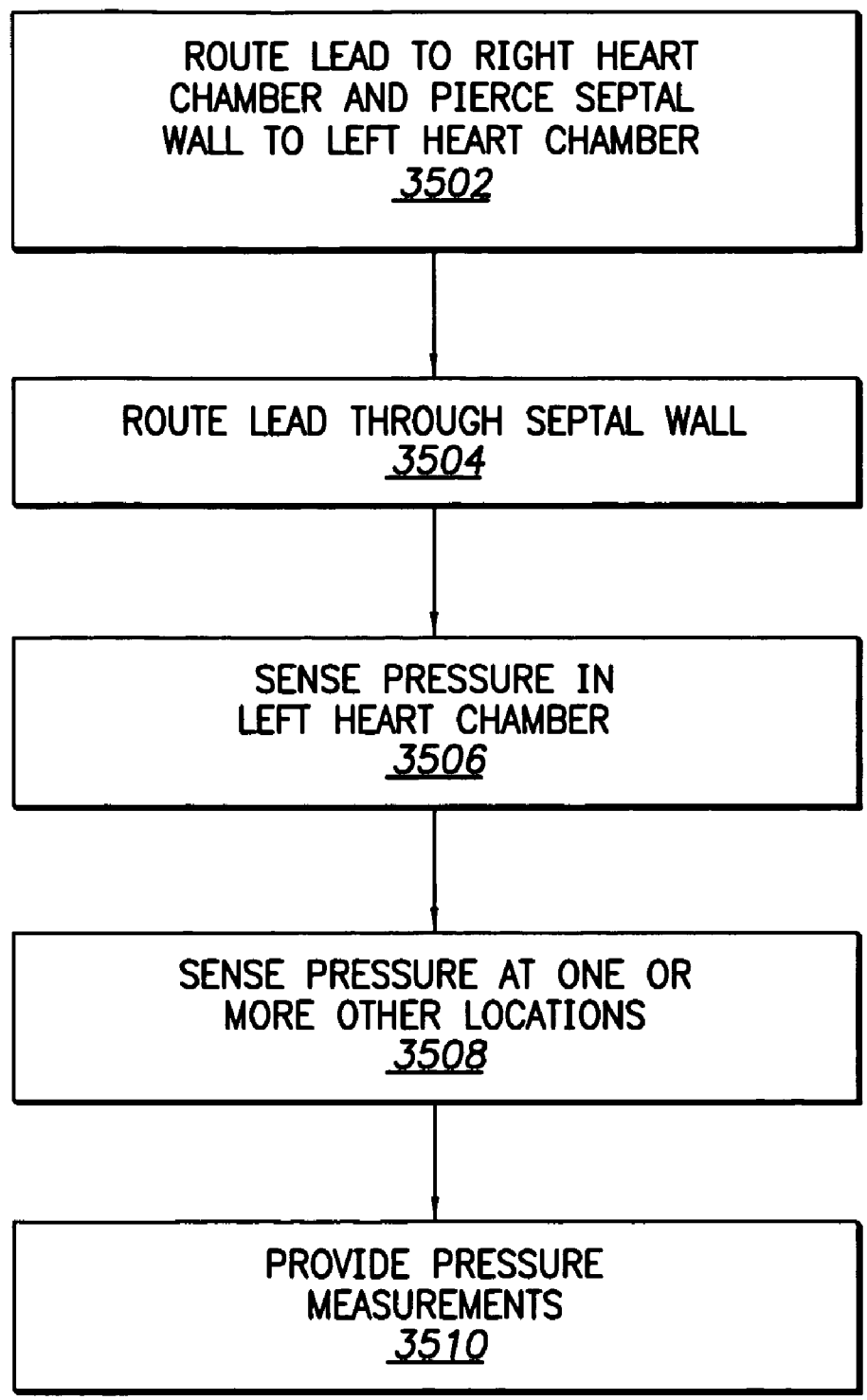
FIG. 35 is a simplified flow chart of one embodiment of pressure measurement operations that may be performed in accordance with the invention.

Referring to FIG. 35, in some embodiments left ventricular pressure may be measured by going through the septum separating the right ventricle and the left ventricle. In this situation a sensor lead may initially be advanced into the right ventricle and the septal wall pierced (block 3502). The lead is then positioned across the septum as discussed above (block 3504). Pressure in the left ventricle (block 3506) and, optionally, one or more other locations (block 3508) may then be sensed to provide a desired pressure measurement (block 3510).

Left ventricular pressure measurement may be most useful for assessing left ventricular function. This information may be used to aide in drug administration, for diagnosis of cardiac dysfunction, or for optimizing the timing such as AV delay, base rate, and V-V timing of an implantable cardiac stimulation device (e.g., a pacemaker). LV pressure and aortic pressure may be used to accelerate or defer shocking the heart during tachyarrhythmias and thus allow for attempts of ATP or to allow more time for confirming the presence of a high mortality risk arrhythmia.

It should be appreciated that the applications discussed herein regarding various embodiments may be applicable to other embodiments as well. For example, the leads described above may be implanted across any wall including the atrial septum and/or the ventricular septum. In addition, the various pressure measurements described above may be measured using the various leads described above.

Different embodiments of the stimulation device described above may include a variety of hardware and software processing components. In some embodiments of the invention, hardware components such as controllers, state machines and/or logic are used in a system constructed in accordance with the invention. In some embodiments, code such as software or firmware executing on one or more processing devices may be used to implement one or more of the described operations.

The components and functions described herein may be connected/coupled in many different ways. The manner in which this is done may depend, in part, on whether and how the components are separated from the other components. In some embodiments some of the connections/couplings represented by the lead lines in the drawings may be in an integrated circuit, on a circuit board or implemented as discrete wires.

The signals discussed herein may take several forms. For example, in some embodiments a signal may be an electrical signal transmitted over a wire while other signals may consist of wireless signals transmitted trough space. In addition, a group of signals may be collectively referred to as a signal herein.

The signals discussed above also may take the form of data. For example, in some embodiments an application program may send a signal to another application program. Such a signal may be stored in a data memory.

In summary, the invention described herein generally relates to an improved cardiac pressure sensing apparatus and method. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of measuring pressure in a patient comprising:
   providing a lead with at least one sensor;
   positioning the lead at a location in the patient at which a thoracic pressure or approximate thoracic pressure may be measured;
   measuring thoracic pressure or approximate thoracic pressure using the at least one sensor;
   measuring pressure at least one other location in the patient to provide a relative thoracic pressure measurement or a relative approximate thoracic pressure measurement;
   wherein positioning the lead comprises:
   routing the lead into the coronary sinus of the patient;
   piercing a coronary sinus wall of the patient; and
   routing the lead through the coronary sinus wall and into a pericardial space of the patient.

2. The method of claim 1 comprising using the at least one sensor to measure pressure in the pericardial sac of the patient to obtain an approximate thoracic pressure measurement.

3. The method of claim 1 comprising routing the lead through the pericardial sac into a thoracic space of the patient and using the at least one sensor to measure thoracic pressure.

* * * * *